United States Patent
Beijersbergen et al.

(10) Patent No.: US 6,255,115 B1
(45) Date of Patent: Jul. 3, 2001

(54) AGROBACTERIUM MEDIATED TRANSFORMATION OF MOULDS, IN PARTICULAR THOSE BELONGING TO THE GENUS *ASPERGILLUS*

(75) Inventors: Alida Godelieve Maria Beijersbergen, Vlaardingen; Paul Bundock, Leiden; Robertus Johannes Gouka; Marcellus Johannes Augustinus de Groot, both of Vlaardingen; Paul Jan Jacob Hooykaas, Leiden, all of (NL)

(73) Assignee: Unilever Patent Holdings BV, Rotterdam (NL)

( * ) Notice: Subject to any disclaimer, the term of this patent is extended or adjusted under 35 U.S.C. 154(b) by 0 days.

(21) Appl. No.: 09/402,628
(22) PCT Filed: Mar. 24, 1998
(86) PCT No.: PCT/EP98/01914
    § 371 Date: Oct. 7, 1999
    § 102(e) Date: Oct. 7, 1999
(87) PCT Pub. No.: WO98/45455
    PCT Pub. Date: Oct. 15, 1998

(30) Foreign Application Priority Data

Apr. 7, 1997 (EP) .................................. 97201022
Dec. 22, 1997 (EP) .................................. 97204062

(51) Int. Cl.[7] .................................. C12N 15/64
(52) U.S. Cl. ............ 435/477; 435/484; 435/254.3; 435/254.4
(58) Field of Search .................. 435/477, 484, 435/254.3, 254.4

(56) References Cited

FOREIGN PATENT DOCUMENTS

91/00920  1/1991  (WO) .
93/12237  6/1993  (WO) .

OTHER PUBLICATIONS

Piers K L et al; "*Agrobacterium tumefaciens*–mediated transformation of yeast." Proceedings of the National Academy of Sciences of the United States of America 93 (4), 1996. 1613–1618. ISSN: 0027–8424, XP000674729 cited in the application, see the whole document.

P.Bundock et al: "Integration of *Agrobacterium tumefaciens* T–DNA in the *Saccharomyces cerevisiae* genome by illegitimate recombination." Proc. Natl. Acad. Sci. USA, vol. 93, No. 26, Dec. 24, 1996, pp. 15272–15275, XP000675824 cited in the application see the whole document.

E. Risseeuw et al.: "Integration of an insertion–type transferred DNA vector from *Agrobacterium tumefaciens* into the *Saccharomyces cerevisiae* genome by Gap repair." Molecular and Cellular Biology, vol. 16, No. 10, Oct. 1996, pp. 5924–5932, XP000675727 cited in the application see the whole document.

M. Ward et al.: "Transformation of *Aspergillus awamori* and A niger by electroporation" Experimental Mycology, vol. 13, 1989, pp. 289–293, XP000675725 cited in the application see the whole document.

P.Bundock et al.: "Trans–kingdom T–DNA transfer from *Agrobacterium tumefaciens* to *Saccharomyces cerevisiae*." The Embo Journal, vol. 14, No. 13, pp. 3206–3214, XP002039985 cited in the application see the whole document.

Beijersbergen A et al.: "Conjugative transfer by the virulence of *Agrobacterium–tumefaciens*." Science (Washington D C) 256 (5061). 1992, 1324–1327. Coden: SCIEAS ISSN: 0036–8075, XP000674721 cited in the application see the whole document.

Hooykaas et al, Annu. Rev. Phytopathol, 32:157–79 (1994).

*Primary Examiner*—James Ketter
(74) *Attorney, Agent, or Firm*—Pillsbury Winthrop LLP

(57) ABSTRACT

The invention relates to Agrobacterium mediated transformation of moulds comprising species of the fungal subdivisions Ascomycotina, Basidiomycotina, Deuteromycotina, Mastigomycotina, and Zygomycotina.

Examples demonstrate the transformation of *Aspergillus awamori* (both protoplasts and conidia), *Aspergillus nidulans*, *Aspergillus niger*, *Colletotrichum gloeosporioides*, *Fusarium solani pisi*, *Neurospora crassa*, *Trichoderma reesei*, *Pleurotus ostreatus* and *Agaricus bisporus* (all conidia), and *Fusarium graminearum* (both conidia and rehydrated freeze dried ATCC material).

Especially for *Aspergillus awamori* the transformation frequency is much higher than with conventional mould transformation techniques.

It has further been found that not only one expressable gene can be introduced into these moulds, but even multiple copies of such gene, which, moreover, can be targeted e.g. in the chromosomal pyrG locus, as exemplified for *A. awamori*. These multiple copies can be of a gene encoding a desired, homologous or heterologous, protein.

23 Claims, 9 Drawing Sheets

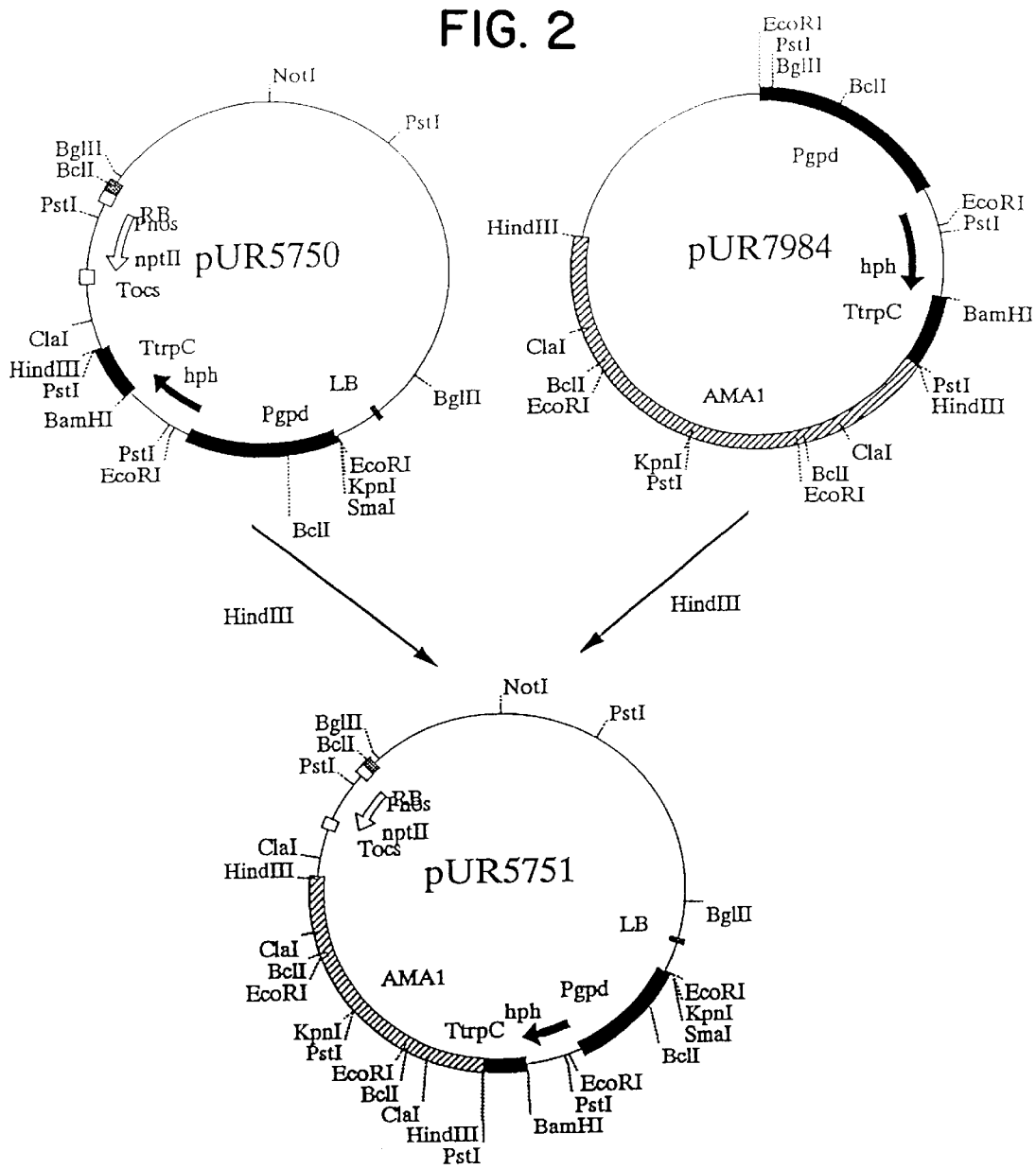

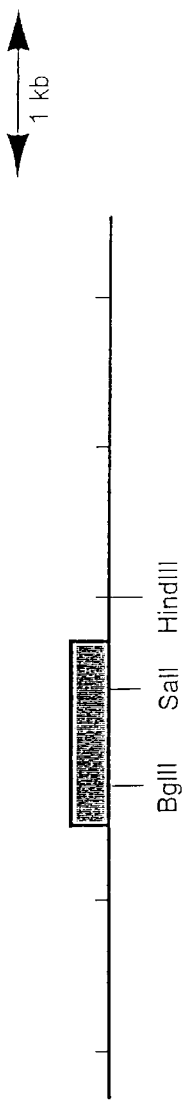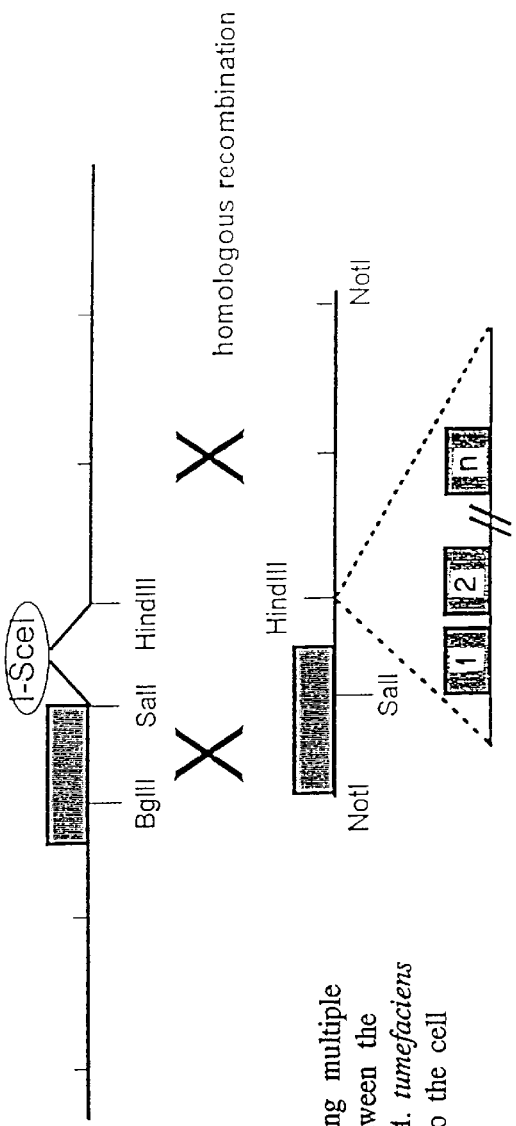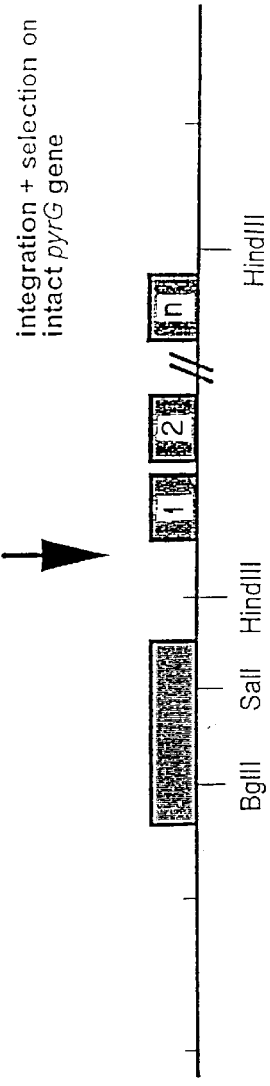
FIG. 3A  wild-type pyrG locus
FIG. 3B  target locus containing an I-SceI restriction site (AWCSCE strain)
FIG. 3C  DNA fragment containing multiple gene copies present between the T-DNA borders in an *A. tumefaciens* vector is introduced into the cell
FIG. 3D  wild-type locus containing multiple gene copies FIG. 8
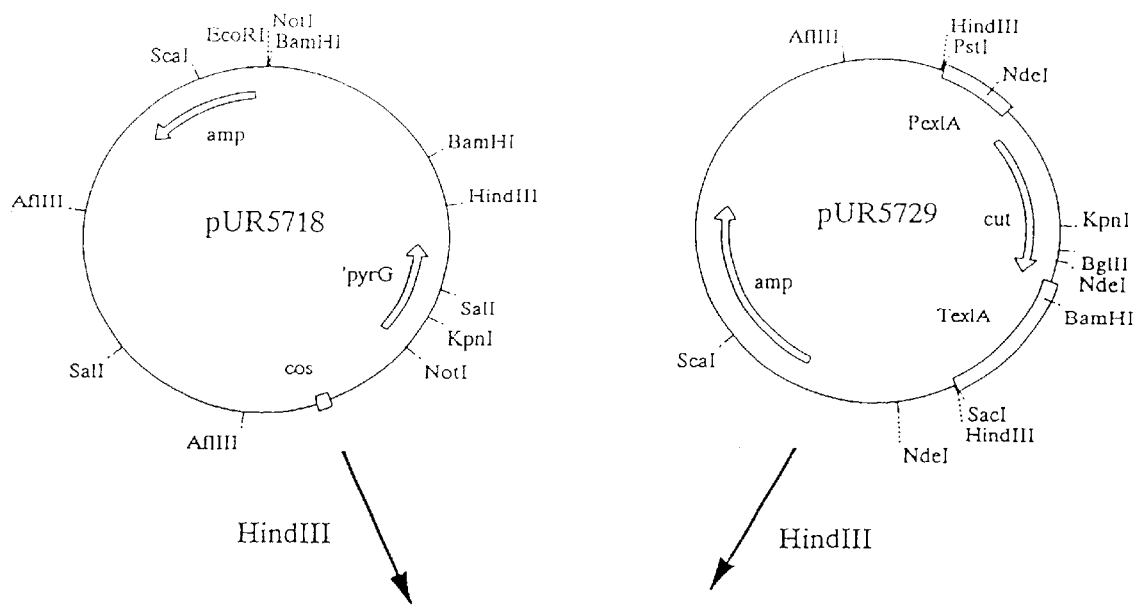
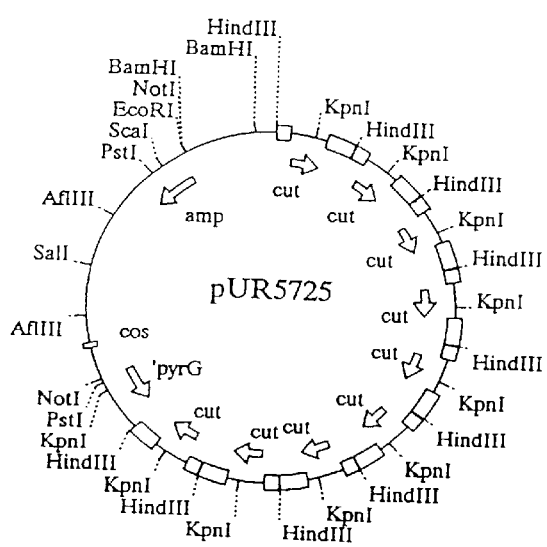

SEQUENCE LISTING

```
<160> NUMBER OF SEQ ID NOS: 5

<210> SEQ ID NO: 1
<211> LENGTH: 18
<212> TYPE: DNA
<213> ORGANISM: Artificial Sequence
<220> FEATURE:
<223> OTHER INFORMATION: Description of Artificial Sequence: ISceI
      endonuclease

<400> SEQUENCE: 1
tagggataac agggtaat                                                  18

<210> SEQ ID NO: 2
<211> LENGTH: 16
<212> TYPE: DNA
<213> ORGANISM: Artificial Sequence
<220> FEATURE:
<223> OTHER INFORMATION: Description of Artificial Sequence: synthetic
      linker (top)

<400> SEQUENCE: 2
aattcatgcg gccgct                                                    16

<210> SEQ ID NO: 3
<211> LENGTH: 16
<212> TYPE: DNA
<213> ORGANISM: Artificial Sequence
<220> FEATURE:
<223> OTHER INFORMATION: Description of Artificial Sequence: synthetic
      linker (bottom)
```

-continued

```
<400> SEQUENCE: 3
agctagcggc cgcatg                                                    16

<210> SEQ ID NO: 4
<211> LENGTH: 16
<212> TYPE: DNA
<213> ORGANISM: Artificial Sequence
<220> FEATURE:
<223> OTHER INFORMATION: Description of Artificial Sequence: MGANotI
      annealing linker

<400> SEQUENCE: 4
caatgcggcc gctaag                                                    16

<210> SEQ ID NO: 5
<211> LENGTH: 24
<212> TYPE: DNA
<213> ORGANISM: Artificial Sequence
<220> FEATURE:
<223> OTHER INFORMATION: Description of Artificial Sequence: MGANotII
      annealing linker

<400> SEQUENCE: 5
catggttacg ccggcgattc ctag                                           24
```

AGROBACTERIUM MEDIATED TRANSFORMATION OF MOULDS, IN PARTICULAR THOSE BELONGING TO THE GENUS *ASPERGILLUS*

This application is the national phase of international application PCT/EP98/01914 filed Mar. 24, 1998 which designated the U.S.

The invention relates to the transformation of moulds, especially of moulds belonging to the genus Aspergillus.

BACKGROUND OF THE INVENTION AND PRIOR ART (1) General transformation techniques for microorganisms In recombinant DNA technology, transformation techniques for bacteria and yeasts are well developed, but transformation frequencies for moulds are relatively low.

For example, in genetic transformation of the bacterium *Escherichia coli* transformation frequencies of about $5 \times 10^8$ transformants/μg vector DNA have been obtained routinely, using a chemical transformation method. Approximately 3.5% of the viable cells became transformed (Hanahan; J. Mol. Biol. 166 (1983) 557–580). More recently, even higher frequencies, of $10^9$ to $10^{10}$ transformants/μg vector DNA, have been reported after high voltage electroporation (Dower et al.; Nucleic Acids Research 16 (1988) 6127–6145). For other bacteria lower transformation frequencies have been described (e.g. Chassy and Flickinger; FEMS Microbiology Letters 44 (1987) 173–177; Miller et al.; Proc. Natl. Acad. Sci. USA 85 (1988) 856–860). For yeasts, transformation frequencies of up to $1 \times 10^7$ transformants per μg vector DNA have been obtained (Meilhoc et al.; Bio/Technology 8 (1990) 223–227 and Gietz et al.; Yeast 11 (1995) 355–360). For moulds, transformation frequencies vary from only 0.1–0.5 transformants/μg vector DNA for *Agaricus bisporus* (Van Rhee et al.; Mol Gen Genet 250 (1996) 252–258), via 5 transformants/μg vector DNA for *Fusarium graminearum* A3/5 (Royer et al.; Bio/Technology 13 (1995) 1479–1483), about 12 transformants/μg vector DNA for *Aspergillus awamori* (Ward et al.; Experimental Mycology 13 (1989) 289–293), and 20–300 transformants/ μg vector DNA for *Aspergillus nidulans* (Yelton et al. Proc. Natl. Acad. Sci. USA 81 (1984) 1470–1474) to about $10^4$ transformants μg vector DNA for *Neurospora crassa* (Volmer and Yanofsky; Proc. Natl. Acad. Sci. USA 83 (1986) 4869–4873).

For review articles on the transformation of moulds reference is made to the articles:

"Transformation in Fungi" by John R. S. Fincham published in Microbiological Reviews (March 1989) 148–170, which gives an outline of the possible transformation methods for fungi, i.e. both yeasts and moulds.

"Genetic engineering of filamentous fungi" by Timberlake, W. E. and Marshall, M. A. Science 244 (1989) 1313–1317.

"Transformation" by David B. Finkelstein (Chapter 6 in the book "Biotechnology of Filamentous Fungi, Technology and Products" (1992) 113–156, edited by Finkelstein and Ball).

From this literature it is clear that several transformation techniques have been developed to transform an increasing number of filamentous fungi. Most transformation protocols make use of protoplasts. Protoplasts can be prepared from hyphal cultures or germinating conidia using Novozyme $234^R$, a multi-enzyme preparation derived from *Trichoderma reesei*. Transformation of protoplasts with DNA is mediated by electroporation or by a combination of $CaCl_2$ and polyethylene glycol (PEG). Some alternative methods avoid the need for making protoplasts, which renders the procedure more rapid and simpler. Intact cells can be transformed using a combination of lithium acetate and PEG, particle bombardment (Lorito et al.; Curr. Genet. 24 (1993) 349–356 and Herzog et al.; Appl. Microbiol. Biotechnol. 45 (1996) 333–337) or also electroporation (Ozeki et al.; Biosci. Biotech. Biochem. 58 (1994) 2224–2227).

In view of the relatively low transformation frequencies of moulds in relation to the transformation frequencies of bacteria and yeasts, a need exists for higher transformation frequencies in moulds.

(2) Plant transformation using Agrobacterium

Another transformation technique developed for plants is based on the use of *Agrobacterium tumefaciens*, which is a gram-negative soil bacterium that causes crown gall tumors at wound sites of infected dicotyledonous plants. During tumor induction Agrobacterium attaches to plant cells and then transfers part of its tumor-inducing (Ti) plasmid, the transferred DNA or T-DNA, to the cell where it becomes integrated in the plant nuclear genome. The T-DNA is flanked by 24 basepair imperfect direct repeats. These direct repeats are also known as "border repeats" or "borders" or "T-DNA borders" or "border sequences" or combinations thereof. The T-DNA contains a set of genes. Expression of a subset of these genes, the onc genes, leads to the production of phytohormones which induce plant cell proliferation and the formation of a tumor. The process of transfer depends on the induction of a set of virulence genes encoded by the Ti plasmid. The transfer system is activated when VirA senses inducing compounds from wounded plants, such as acetosyringone (AS). Via the transcriptional activator VirG, the remaining vir loci are activated and a linear single-stranded DNA, the T-strand, is produced following nicking of the border repeats by a virD1/D2 encoded site-specific endonuclease. The VirD2 protein remains covalently attached to the 5' terminus. The T-strand is coated by the single-strand binding protein VirE and the resulting complex is transferred to the plant cell. Although the mechanism by which the T-DNA complex is transported from the bacterium into the plant cell is not well understood, it is thought that the T-DNA complex leaves the Agrobacterium cell through a transmembrane structure consisting of proteins encoded by the virB operon. For extensive reviews on *Agrobacterium tumefaciens* transformation see Hooykaas and Schilperoort (Plant Molecular Biology 19 (1992) 15–38) and Hooykaas and Beijersbergen (Annu. Rev. Phytopathol. 32 (1994) 157–179). The ability of *Agrobacterium tumefaciens* to transfer its T-DNA into the plant cell, where it is stably integrated into the nuclear genome, has lead to a widespread use of this organism for gene transfer into plants and plant cells. In order to allow the regeneration of plants after *Agrobacterium tumefaciens* transformation the onc genes in the T-region have been deleted, which resulted in a disarmed or non-oncogenic T-DNA. Two types of vector systems have been developed for plant transformation. First a binary system, in which new genes are cloned in between the T-DNA borders of a plasmid containing an artificial T-DNA This plasmid is subsequently introduced into an Agrobacterium strain harbouring a Ti plasmid with an intact vir region but lacking the T region (Hoekema et al.; Nature 303 (1983) 179–180 and Bevan; Nucl. Acids Res. 12 (1984) 8711–8721). Secondly a co-integrate system, in which new genes are introduced via homologous recombination into an artificial T-DNA already present on a Ti plasmid with an intact vir region (Zambryski et al.; EMBO-J. 2 (1983) 2143–2150).

A wide variety of plant species have been transformed using such systems. This includes many agriculturally important dicotyledonous species such as potato, tomato, soybean, sunflower, sugarbeet and cotton (for a review see Gasser and Fraley; Science 244, (1989) 1293–1299). Although Agrobacterium transformation of monocotyledonous plants seemed to be impossible for a long time, nowadays several species such as maize (Ishida et al.; Nature-Biotechnology 14 (1996) 745–750) and rice (Aldemita and Hodges; Planta 199 (1996) 612–617) have been transformed using Agrobacterium.

One of the reasons why the method has found wide use in plant transformation is its high transformation frequency. For instance in co-cultivation experiments with tobacco protoplasts about 25% percent of the microcalli, that were regenerated from protoplasts after co-cultivation with Agrobacterium (on average 20%), were transformed (Depicker et al.; Mol. Gen. Genet. 201 (1985) 477–484 and Van den Elzen et al.; Plant Molecular Biology 5 (1985) 149–154). This means that up to about 5% of the cells are transformed. Furthermore, the method is much easier compared with other plant transformation methods using naked DNA. It is applicable to intact plant tissues such as segments of leaves, stem, root and tubers as well as protoplasts. Additionally, the method has the advantage that only the T-DNA comprising the foreign DNA to be introduced is integrated into the plant genome. The vector DNA sequences required for replication and selection of the vector in the bacterium are not transported from the bacterium to the plant cell. Thus it is a relatively clean transformation method.

Another Agrobacterium species, *Agrobacterium rhizogenes*, possesses a similar natural gene transfer system.

(3) Transformation of micro-organisms using Agrobacterium

In addition to the many publications on transformation of plants using *Agrobacterium tumefaciens*, recently the results of some investigations on the use of *Agrobacterium tumefaciens* for transforming micro-organisms were published. Beijersbergen et al. (Science 256 (1992) 1324–1327) demonstrated that the virulence system of *A. tumefaciens* can mediate conjugative transfer between agrobacteria, which only relates to transformation of different strains of the same species. Bundock et al. (EMBO-J. 14 (1995) 3206–3214) reported on successful transformation of yeast by this soil bacterium. This result was subsequently confirmed by Piers et al. (Proc. Natl. Acad. Sci. USA, 93 (1996) 1613–1618). Both groups used DNA sequences from *S. cerevisiae* such as the yeast 2 $\mu$ origin (Bundock et al.; EMBO-J. 14 (1995) 3206–3214) or yeast telomeric sequences and the ARS1 origin of replication (Piers et al.; Proc. Natl. Acad. Sci. USA, 93 (1996) 1613–1618) in order to stabilize the T-DNA in yeast. Very recently, Risseeuw et al. (Mol. Cell. Biol. 16 (1996) 5924–5932) and Bundock & Hooykaas (Proc. Natl. Acad. Sci. USA, 93 (1996) 15272–15275) reported results on the mechanism of T-DNA integration in *S. cerevisiae*.

The data made available by these publications show that the transformation of micro-organisms by *Agrobacterium tumefaciens* is much less effective than that of plants. As mentioned above, in plants up to about 5% of the cells have been transformed, whereas for yeast much lower ratios of transformed cells/recipient cells are reported, namely $3\times10^{-3}$ (Piers et al., Proc. Natl. Acad. Sci. USA, 93 (1996) 1613–1618) and $3.3\times10^{-6}$ (Bundock et al. EMBO-J 14 (1995) 3206–3214).

Additionally, *A. tumefaciens* transformation of microorganisms proved to be less efficient than traditional transformation techniques for micro-organisms. Usually the transformation frequency for naked DNA transfer is depicted as the number of transformants per $\mu$g vector DNA, whereas the transformation frequency for *A. tumefaciens* transformation is often expressed as the number of transformed cells that can be obtained in relation to the number of recipient cells. In a prior publication on conventional transformation of yeast (Gietz et al.; Yeast 11, (1995) 355–360) both figures on transformants/$\mu$g vector DNA and figures on transformed cells per recipient cell are given, which gives a link between the two methods of calculating the transformation frequency.

Gietz et al. determined that with their LiAc/SS-DNA/PEG procedure a maximum of about 4% of the yeast cells in the reaction could be transformed, i.e. a transformation frequency of up to $4\times10^{-2}$. From FIG. 1A and the corresponding description of this publication one can calculate that this 4% corresponds with $8\times10^5$ transformants/$\mu$g vector DNA. For *A. tumefaciens* transformation of yeast the maximal reported transformation frequencies are $3\times10^{-3}$ (Piers et al.; Proc. Natl. Acad. Sci. USA, 93 (1996) 1613–1618) and $3.3\times10^{-6}$ (Bundock et al.; EMBO-J. 14 (1995) 3206–3214), which is a factor of about 10 or 10,000, respectively, lower than the maximum transformation frequency (4%) of yeast with naked DNA reported by Gietz et al. Thus based on this evidence *A. tumefaciens* does not seem to be an additional promising tool for the transformation of micro-organisms, because the transformation frequencies obtained with *A. tumefaciens* are much lower than with the conventional transformation methods of yeast.

SUMMARY OF THE INVENTION

The invention is based on the idea of using Agrobacterium for transforming moulds. Notwithstanding the just indicated low transformation frequencies obtained with only one yeast species, namely *Saccharomyces cerevisiae*, the inventors decided to investigate the *Agrobacterium tumefaciens* mediated transformation of the mould *Aspergillus awamori*. The latter is an important mould for the production of enzymes, proteins and metabolites, but it has the disadvantage that the conventional mould transformation techniques are relatively inefficient as shown by the figures given above (see Ward et al.).

Surprisingly, it was found that the plant transformation technique with *Agrobacterium tumefaciens* could be applied successfully with the mould *Aspergillus awamori*. After some experiments a transformation frequency of more than 7000 transformants per $10^7$ recipient cells was obtained, which is about 400 times the transformation frequency obtained with conventional transformation (see Example 1 below). Subsequently, this technique was also applied successfully to a wide variety of moulds, including *Aspergillus niger*, *Aspergillus nidulans*, *Fusarium solani pisi* (CBS 230.34), *Fusarium graminearum* (ATCC 20334), *Trichoderma reesei* (CBS 383.78), *Colletotrichum gloeosporioides* (CBS 862.70), *Neurospora crassa* (CBS 195.57), *Pleurotus ostreatus* (strain Somycel 3015; purchased from "Proefstation voor de Champignoncultuur"), and *Agaricus bisporus* (commercial strain Horst U1 also purchased from "Proefstation voor de Champignoncultuur"). These moulds belong to different taxonomic backgrounds as shown in Table 1 below. Table 2 below gives the approximate number of genera and species within each division of the Eumycota. The subdivision Mastigomycotina comprises the Chytridiomycetes and the Oomycetes. As described in Example 11, direct transformation of *Agaricus bisporus* strain Horst U1 has not been carried out before. Thus the invention provides for the first time a direct transformation of this commercially important Horst U1 strain.

Thus in a broad sense the invention relates to the transformation of moulds, also known as filamentous fungi. The Examples given below represent the three major subdivisions moulds has not been optimized. Based on the experience with Agrobacterium transformation in plants, it is likely that the transformation frequencies can be increased further. Many of these moulds are important in industry, agriculture and basic biological research.

For example *Aspergillus awamori, Aspergillus niger, Trichoderma reesei* and *Fusarium graminearum* have shown to be attractive hosts for large scale production of homologous and heterologous proteins (Van den Hondel et al.; "Heterologous gene expression in filamentous fungi" (Chapter 18) in the book "More Gene Manipulations in Fungi" (1991) 397–428, edited by Bennett and Lasure; Verdoes et al.; Appl. Microbiol. Biotechnol 43 (1995) 195–205; Royer et al.; Bio/Technology 13 (1995) 1479–1483). They have the

TABLE 1

Arrangement of the Fungal Kingdom including species transformed by Agrobacterium.

| Division | Subdivision | Class | Order | Family | Species |
|---|---|---|---|---|---|
| Myxomycota | | | | | |
| Eumycota | Mastigomycotina | | | | |
| | Zygomycotina | | | | |
| | Ascomycotina | Ascomycetes | Eurotiales | Eurotiaceae | *Aspergillus niduians* |
| | | | Sphaeriales | Sordariaceae | *Neurospora crassa* |
| | Basidiomycotina | Homobasidiomycetes | Agaricales | Agaricaceae | *Agaricus bisporus* |
| | | | | Tricholomataceae | *Pleurotus ostreatus* |
| | Deuteromycotina | Deuteromycetes | Hyphomycetes | | *Aspergillus niger* |
| | | | | | *Aspergillus awamori* |
| | | | | | *Fusarium solani* |
| | | | | | *Fusarium graminearum* |
| | | | | | *Trichoderma reesei* |
| | | | Coelomycetes | Melanconiaceae | *Colletotrichuni gloeosporioides* |

References:
-Ainsworth, Sparrow and Sussman; The Fungi, Vol. IV A + B (1973)
-Gams, Van der Aa, Van der Plaats-Niterink, Samson and Stalpers; CBS Course of Mycology, 3rd edition (1987)

of the Emuycota which together from about 95% of the mould species (see Table 2).

TABLE 2

Approximate number of genera and species in each division of the Eumycota (as published by O'Donnell and Peterson in Chapter 2 of the book "Biotechnology of Filamentous Fungi, Technology and Products" (1992) 7–33, edited by Finkelstein and Ball).

| Division | No. and percentage genera | No. and percentage species |
|---|---|---|
| Mastigomycotina | 190 (3.2) | 1170 (1.8) |
| Zygomycotina | 145 (2.5) | 765 (1.2) |
| Ascomycotina | 2720 (46.6) | 28650 (45.0) |
| Basidiomycotina | 1104 (18.9) | 16000 (25.2) |
| Deuteromycotina | 1680 (28.8) | 17000 (26.8) |

For *Colletotrichum gloeosporioides* the method of the invention is about 5 to 10 times better than the published frequency for naked DNA transfer (see Example 5). Several of other tested moulds, such as *Fusarium graminearum* (see Example 7), *Neurospora crassa* (see Example 8) *Trichoderma reesei* (see Example 9), and *Pleurotus ostreatus* (see Example 10), gave transformation frequencies after Agrobacterium transformation that are similar to the optimal naked DNA transfer methods. The moulds *Aspergillus nidulans, Aspergillus niger* and *Fusarium solani* gave transformation frequencies after Agrobacterium transformation that are lower than the frequencies for naked DNA transfer. For the Aspergillus species this is presumably caused by problems with the selection of transformants (see Examples 3 and 4). It should be noted that transformation of the other capacity to secrete substantial amounts of protein into the medium, large scale fermentation is generally well established and they have a GRAS (Generally Recognized As Safe) status, which makes it possible to use these species in the food and food-processing industry. Moreover, the mould *Fusarium graminearum* A 3/5, the Quorn® myco-protein fungus, has also been used as a commercial human food source in the UK for over 10 years (Royer et al.; Bio/Technology 13 (1995) 1479–1483).

The moulds *Fusarium solani* and *Colletotrichum gloeosporioides* are fungal pathogens (Marek et al.; Curr Genet 15 (1989) 421–428; Hwang et al.; The Plant Cell 7 (1995) 183–193).

Both *Aspergillus nidulans* and *Neurospora crassa* have been important organisms for basic research into genetic mechanisms, biochemical pathways and cellular physiology (Vollmer and Yanofsky; Proc. Natl. Acad. Sci. USA 83 (1986) 4869–4873; The book "Aspergillus: 50 year on" (1994) edited by Martinelli and Kinghorn).

The mushrooms *Pleurotus ostreatus* and *Agaricus bisporus* are edible and commercially important. Successful transformations using a process according to the invention are described in Examples 10 and 11.

It has further been found that not only one expressable gene can be introduced into these moulds, but even multiple copies of such gene, which, moreover, can be targeted e.g. in the chromosomal pyrG locus. These multiple copies can be of a gene encoding a desired, homologous or heterologous, protein.

This embodiment of the invention is illustrated in Example 12.

BRIEF DESCRIPTION OF THE DRAWINGS

FIG. 2 shows the construction of plasmid pUR5751. Explanation of the abbreviations used in the construction scheme:
AMA1=the plasmid replicator AMA1 from *Aspergillus nidulans*

FIG. 3 shows the experimental design of the process for site-directed integration of multiple copies of a gene in the mould *A. awamori*.

FIG. 8 shows the construction of cosmid pUR5725.

DETAILED DESCRIPTION OF THE INVENTION

Figure 1:
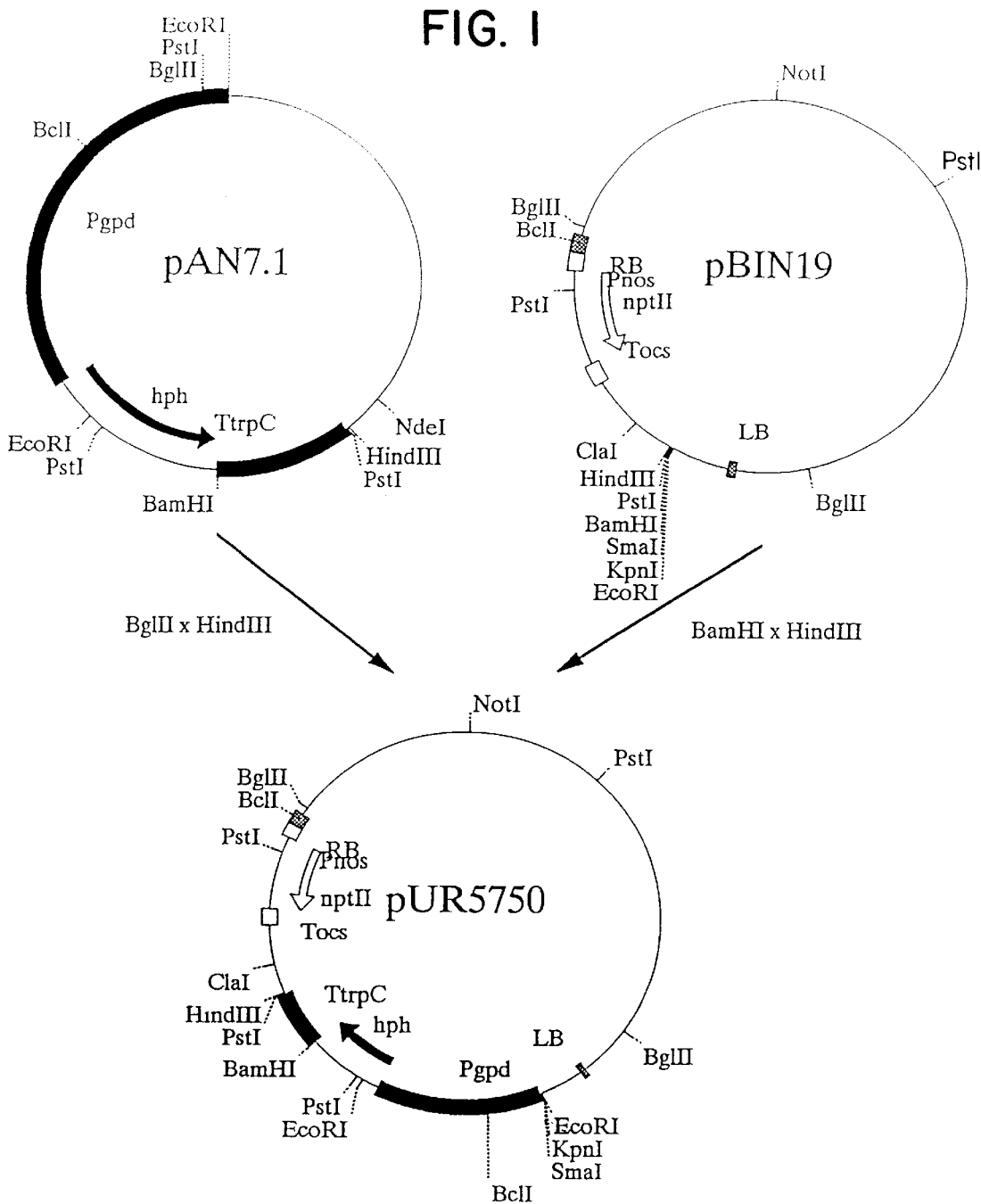
FIG. 1 shows the construction of plasmid pUR5750. Explanation of the abbreviations used in the construction scheme:
RB=Right T-DNA Border,
Pnos=Promoter sequences of the nopaline synthase gene,
nptII=coding region of the neomycin phosphotransferase II gene from Tn5,
Tocs=Terminator sequences of the octopine synthase gene,
TtrpC=Terminator sequences from the *A. nidulans* trpC gene,
hph=coding region of the hygromycin phosphotransferase gene from *E. coli*,
Pgpd=Promoter sequences of the *A. nidulans* gpd gene,
LB=Left T-DNA Border.

The invention provides a process for producing a transformed mould, characterised in that
(1) a DNA fragment containing at least one expressable gene to be introduced into a mould is first cloned into a vector of *Agrobacterium tumefaciens* between the T-DNA borders present in that vector;
(2) the vector containing the DNA fragment between the T-DNA borders is introduced into an *Agrobacterium tumefaciens* strain containing a vir region in its DNA;
(3) release of T-DNA containing said DNA fragment from said *Agrobacterium tumefaciens* by addition of a vir-inducing compound, and the *Agrobacterium tumefaciens* strain is incubated with the mould to be transformed; and
(4) the transformed mould is selected from the untransformed mould depending on the characteristics of the introduced DNA or its expression product, and optionally the transformed mould is cultured.

The selection of the transformed mould can be carried out by using a selectable marker. For example, such selectable marker is a characteristic of a naturally-occurring, wild-type mould strain, while the mould strain to be transformed is a mutant strain thereof, deficient in said selectable marker, e.g. the orotidine-5'-phosphate decarboxylase gene (pyrG gene) which is present in wild-type *Aspergillus awamori*. Suitable selectable markers include antibiotic resistance markers, genes for utilisation of metabolites not usually utilized in that mould strain, and genes producing an easily-assayable product.

Sometimes the DNA introduced into the mould can be used as the selectable marker. For example, when the introduced DNA is expressed, it can result in a product not produced in the non-transformed mould, but more or less easily assayable. Or the presence or absence of the DNA can be determined by applying PCR techniques.

Preferably the mould belongs to the fungal division of Eumycota, more preferably to one of the fungal subdivisions Ascomycotina including the species *Aspergillus nidulans* and *Neurospora crassa*, Basidiomycotina including Bjerkandera, Coprinus, Coriolus species, and the species *Agaricus bisporus*, *Flammulina velutipes* (Enokitake), *Lentinus edodes* (Shiitake), *Phanerochaete chrysosporium*, *Schizophyllum commune*, *Tricholoma matsutake*, and *Pleurotus ostreatus*, Deuteromycotina including Beauveria and Metarhizium species (suitable as biological control agents against insects), Acremonium and Penicillium species (suitable for production of antibiotics) and the species *Aspergillus niger*, *Aspergillus awamori*, *Fusarium solani*, *Fusarium graminearum*, *Trichoderma reesei*, and *Colletotrichum gloeosporioides*, Mastigomycotina comprising the Oomycetes including Achlya (suitable for production of pharmaceutically active proteins), Phytophtora, Pythium, and Plasmopara species, and the Chytridiomycetes including Rhizophydium and Rhizophlyctis species, and Zygomycotina including Mucor and Rhizopus species.

In a preferred embodiment of the invention a process is provided, in which the DNA fragment contains multiple copies of a desired gene. Alternatively the DNA fragment may contain at least one copy of several genes, or it may contain one or more copies of a fused gene.

According to another preferred embodiment of the invention the DNA fragment is integrated in a selected locus of the mould genome. An example of such selected locus is the pyrG locus of the mould genome (which is known as the pyrA locus for *A. niger* and the pyr4 locus for *Neurospora crassa*). This enables the production of a transformed mould that does not contain any unwanted bacterial DNA sequence including a T-DNA border.

Thus the invention provides a transformed mould obtainable by Agrobacterium mediated transformation according to the invention not comprising any unwanted bacterial DNA sequence including a T-DNA border. Such transformed mould can be used in a process for culturing a transformed mould in order to produce a desired protein.

According to another embodiment of the invention a process is provided, in which the DNA fragment is randomly integrated in the mould genome, as well as a transformed mould obtainable by Agrobacterium mediated transformation, which comprises one or more parts of T-DNA border sequences, and a process for culturing such transformed mould in order to produce a desired protein.

The use of supervirulent *A. tumefaciens* strains is preferred, because they give a relatively high transformation frequency. Such strains, the use thereof and vectors for making such strains are described in the literature; see Jin et al. (J. Bacteriology 169 (1987) 4417–4425 & Molecular Microbiology 7 (1993) 555–562), Raineri et al. (BIO/TECHNOLOGY 8 (January 1990) 33–38) and Ishida et al. (Nature Biotechnology 14 (1996) 745–750) for plant transformation, and Piers et al. (Proc. Natl. Acad. Sci. USA, 93 (1996) 1613–1618) for yeast transformation.

The transformation can be performed by a binary system or by co-integration in a similar way as is known for plant transformation as discussed above in the section on (2) Plant transformation using Agrobacterium.

All types of mould tissue can be used including protoplasts, conidio spores, germinating spores, mycelia, and pellets, of which protoplasts, conidia and rehydrated freeze dried culture material are exemplified below.

Advantages of the Agrobacterium mediated transformation of moulds include it is a "food-grade" method resulting in a mould strain without residues of bacterial antibiotic resistance markers or other bacterial sequences like origins of replication, larger parts of DNA can be introduced. In contrast to the older method of naked DNA mould transformation whereby up to about 40 kb DNA can be introduced, with Agrobacterium mediated plant transformation at least 150 kb of foreign DNA was introduced into the plant genome (Hamilton et al.; Proc. Natl. Acad. Sci. USA 93 (1996) 9975–9979).

EXAMPLES

The invention is exemplified by the following Examples 1–12 preceded by a description of the Materials and Methods that were used. These Examples show the transformation of A. awamori both protoplasts (Ex. 1) and conidia (Ex. 2), A. nidulans conidia (Ex. 3), A. niger conidia (Ex. 4), Colletotrichumi gloeosporioides (Ex. 5), Fusarium solani pisi conidia (Ex. 6), Fusarium graminearum both conidia and rehydrated freeze dried ATCC material (Ex. 7), Neurospora crassa conidia (Ex. 8), Trichoderma reesei conidia (Ex. 9), Pleurotus ostreatus conidia (Ex. 10), and Agaricus bisporus conidia (Ex.11). Further, Example 12 shows the transformation of A. awamori by introducing into the pyrG locus multiple copies of a cutinase expression cassette.

MATERIALS AND METHODS

Bacterial and Mould Strains

For bacterial cloning the *Escherichia coli* strain DH5α (geno-type: F−, endA1, hsdR17 ($r_k^-m_k^+$), supE44, thi–1, lambda−, recA1, gyrA96, relA1, Δ(argF-lacIZYA)U169, deoR (phi80d-(lacz)ΔM15); Hanahan; J. Mol. Biol. 166 (1983) 557–580) was used. The *Agrobacterium tumefaciens* strain LBA1100 was used for the transformation of moulds (Beijersbergen et al., 1992, Science, 256, p. 1324–1327). The mould strains *Aspergillus awamori* #40 (a derivative of *A. awamori* CBS 115.52 also mentioned in WO 93/12237, page 9 line 13), *Aspergillus niger* (strain N402, a cspA1 (short conidiophores) mutant of *Aspergillus niger* var. *niger* ATCC9029, CBS 120.49 described in UNILEVER's WO 91/19782) *Aspergillus nidulans* (Lab collection URL-VL), *Fusarium solani pisi* (CBS 230.34), *Fusarium graminearum* (ATCC 20334), *Trichoderma reesei* (CBS 383.78), *Colletotrichum gloeosporioides* (CBS 862.70), *Neurospora crassa* (CBS 195.57), and *Pleurotus ostreatus* strain Somycel 3015 and *Agaricus bisporus* strain Horst U1 (both purchased from "Proefstation voor de Champignon-cultuur", P.O. Box 6042, 5960 AA Horst, The Netherlands), were used as the recipient in transformations with *Agrobacterium tumefaciens*.

The preparation of *A. awamori* #40 (also known as *A. niger* var. *awamori* #40) was described in WO 91/19782 on page 13, lines 29–39, which read:

"The production level of the *A. niger* var. *awamori* transformants, however, can be further increased by using suitable *A. niger* var. *awamori* mutant strains, such as *A. niger* var. *awamori* #40, which produces clearly more xylanase than the wild type strain.

The mutant *A. niger* var. *awamori* #40 has been obtained by mutagenesis of *A. niger* var. *awamori* spores and selection for xylanase production. In bran medium the "xylA"*A. niger* var. *awamori* #40 transformant produced 190 000 U xylanase, which is a considerable increase over the best producing *A. niger* var. *awamori* transformant.

In this specification the following endonuclease restriction sites are used:

| giving staggered ends | | giving blunt ends | |
|---|---|---|---|
| AflII | C↓TTAAG | SmaI | CCC↓GGG |
| BamHI | G↓GATCC | | |
| BglII | A↓GATCT | | |
| EcoRI | G↓AATTC | | |
| HindIII | A↓AGCTT | | |
| KpnI | GGTAC↓C | | |
| NotI | GC↓GGCCGC | | |
| PstI | CTGCA↓G | | |
| SacI | GAGCT↓C | | |
| SalI | G↓TCGAC | | | and the rare-cutting restriction endonuclease from *Saccharomyces cerevisiae* I-SceI 18 bp:

5'-TAGGGATAACAGGGTAAT-3' SEQ ID NO:1

Plasmid Construction

Plasmid pUR5750 (see FIG. 1) was constructed by cloning a 4 kb BglII/HindIII fragment, which is present on the vector pAN7.1 (Punt et al.; Gene 56 (1987) 117–124) and contains the promoter from the *A. nidulans* gpd gene fused to the coding region of the *E. coli* hph gene and followed by terminator sequences from the *A. nidulans* trpC gene, into the BamHI/HindIII sites of the binary vector pBIN19 (Bevan, M.; Nucleic Acids Res. 22 (1984) 8711–8721).

Plasmid pUR5751 (see FIG. 2) was constructed by cloning the plasmid replicator AMA1 from *Aspergillus nidulans* (Aleksenko and Clutterbuck; Molecular Microbiology 19 (1996) 565–574) as a 5.3 kb HindIII fragment from the plasmid pUR7984 into the HindIII site of pUR5750. pUR7984 was obtained by cloning the 5.3 kb AMA1 HindIII fragment from pHELP1 (provided by Clutterbuck) into the HindIII site of pAN7.1. The 5.3 kb AMA1 HindIII fragment is the fragment between the HindIII site at position 367 and the HindIII site at position 5620 of the sequence deposited in the EMBL/GenBank/DDBJ Nucleotide Sequence Data Library under Ac. no. X78051.

The Agrobacterium strain LBA1100, first described by Beijersbergen et al. (Science 256 (1992) 1324–1327) and referred to in several later publications, was electroporated with the constructs pUR5750 and pUR5751 according to Mozo and Hooykaas (Plant Mol. Biol. 16 (1991) 917–918).

This Agrobacterium strain LBA1100 has been deposited on Mar. 27, 1997 under the Budapest Treaty at the Centraal-bureau voor Schimmelcultures in Baarn, The Netherlands (No. CBS 634.97).

Transformation Experiments

The Agrobacterium strain containing the binary vector pUR5750 was grown at 29° C. overnight on LB plates containing the appropriate antibiotics at the following concentrations: kanamycin, 100 μg/ml; spectinomycin, 250 μg/ml; rifampicin, 20 μg/ml. A single colony was streaked on a minimal medium plate. Minimal medium (MM) contains per litre: 10 ml K-buffer pH7.0 (200 g/l $K_2HPO_4$, 145 g/l $KH_2PO_4$), 20 ml M-N (30 g/l $MgSO_4 \cdot 7H_2O$, 15 g/l NaCl), 1 ml 1% $CaCl_2 \cdot 2 H_2O$ (w/v), 10 ml 20% glucose (w/v), 10 ml 0.01% $FeSO_4$ (w/v), 5 ml spore elements (100 mg/l $ZnSO_4 \cdot 7 H_2O$, 100 mg/l $CuSO_4 \cdot 5 H_2O$, 100 mg/l H$_3$BO$_3$, 100 mg/l MnSO$_4$.H$_2$O, 100 mg/l Na$_2$MoO$_4$.2 H$_2$O) and 2.5 ml 20% NH$_4$NO$_3$ (w/v) (Hooykaas et al.; J. Gen. Microbiol. 110 (1979) 99–109) bacto-agar at 15 g/l and the appropriate antibiotics. The plates were incubated at 29° C. for 1 to 2 days. Several colonies were inoculated in minimal medium containing the appropriate antibiotics and grown at 29° C. overnight. After dilution of Agrobacterium cells to an OD$_{660\ nm}$ of approximately 0.15 in induction medium the culture was grown for 6 hours at 29° C. The induction medium (IM) differs from minimal medium in that the 10 ml 20% glucose (w/v) was replaced by 10 mM glucose and 40 mM MES (ex Sigma) (pH5.3), 0.5% glycerol (w/v), and 200 µM acetosyringone (AS) were added. In order to confirm that transformation of the moulds by Agrobacterium is dependent on T-DNA transfer, a negative control was included in which the vir inducer AS was omitted. Conidia were obtained by growing the mould strains at room temperature on a nitrocellulose filter (Hybond-N, Amersham) placed on a PDA (Potato Dextrose Agar) plate for several days and subsequently washing the filters with physiological salt solution. Protoplasts of A. awamori were prepared as described by Punt and Van den Hondel (Methods in Enzymology 216 (1993) 447–457). For transformation of protoplasts, a 100 µl aliquot containing 10$^6$ to 10$^7$ protoplasts was mixed with 100 µl of the Agrobacterium culture. For transformation of conidia, conidia were diluted in physiological salt solution at a concentration of 10$^6$, 10$^7$ or 10$^8$ conidia/ml and 100 µl was mixed with 100 µl of the Agrobacterium culture. Subsequently, the mixtures were plated on nitrocellulose filters placed on IM plates (IM medium with 15 g/l bacto-agar) containing 5 mM glucose and incubated at room temperature or 29° C. for 2, 3, 5 or 6 days (as indicated in the Examples). The negative control samples were incubated on IM plates in which the vir inducer AS was omitted. Hereafter, the filters were transferred to Aspergillus minimal medium plates (Bennett and Lasure, Growth media In: Bennett and Lasure (eds) More gene manipulations in fungi, Academic Press, San Diego (1991) 441–458) or PDA plates containing 200 µM cefotaxim to kill the Agrobacterium cells and hygromycin (for concentrations see Examples) to select for trans formants.

DNA Isolation and Southern Analysis

Southern analysis was performed to confirm at a molecular level that the mould cell had been transformed and the desired DNA had been integrated into the genome. To obtain mycelium material for a genomic DNA isolation, approximately 10$^8$ mould conidia were inoculated in 50 ml of Aspergillus minimal medium supplemented with 0.5% yeast extract and incubated for a period ranging from 22 hours to 3 days at 30° C. in a shaker at 200 rpm. The mycelium was harvested through Miracloth® (Calbiochem) and snap frozen in liquid N$_2$. Frozen samples were ground to a fine powder using a Mikro-DismembratorR (ex Braun Biotech International) for 1 minute at 1750 rpm. Mould genomic DNA was isolated using Qiagen genomic tips (cat. no. 10223) and a protocol for genomic DNA purification from filamentous fungi provided by the supplier. The step for digestion of cell wall material was omitted. Approximately 2.5 µg of DNA was digested with BglII or HindIII (4 Units/µg) for 16 hours and separated on a 0.8% agarose TBE gel. DNA was transferred to a Hybond N membrane by capillary blotting (overnight) and the membrane was (pre-)hybridized according to the Hybond protocol. Either the 4 kb BglII/HindIII fragment from pAN7.1 described above, which contains part of the vector, or the 0.8 kb BamHI/EcoRI fragment from pAN7.1, which contains part of the E. coli hph gene, was used as a probe for Southern blots. A DNA probe labelled with α$^{32}$P-dCTP was obtained using the RTS RadPrime DNA Labelling System from GibcoBRL (cat. no. 10387-017).

Example 1

Transformation of A. awamori Protoplasts

For protoplast isolation, a shake flask containing 200 ml of MM medium including 0.5% yeast extract was inoculated with 10$^6$ conidia/ml of A. awamori and incubated for 18 hours at 30° C. in a shaker at 200 rpm. Mycelium was harvested through sterile Mirocloth® and washed with ice-cold 0.6 M MgSO$_4$. The mycelium was resuspended in OM medium (per litre: 500 ml 2.4 M MgSO$_4$, 480 ml H$_2$O, 16.8 ml 0.5 M Na$_2$HPO$_4$, 3.2 ml 0.5 M NaH$_2$PO$_4$, pH 5.8–5.9) at 5 ml/g mycelium. Subsequently, 5 mg Novozym 234® and 6 mg BSA were added per g mycelium. Protoplasting was allowed to proceed for 1–2 hours at 30° C. in a shaker at 80–100 rpm. The formation of protoplasts was checked using a light microscope. Protoplasts were filtered through sterile Miracloth® and the sample was divided in 30 ml aliquots in falcon tubes. STC (1.2 M sorbitol, 10 mM Tris/HCl pH 7.5, 50 mM CaCl$_2$.2 H$_2$O) was added to bring the volume up to 50 ml and the protoplasts were harvested by centrifugation at 2000 rpm for 10 minutes at 4° C. The protoplasts were washed again in 50 ml STC and resuspended in STC at a concentration of approximately 10$^8$ protoplasts/ml. In order to compare the frequency of transformation using A. tumefaciens with PEG transformation, PEG transformations were also performed. Five µg of pAN7.1 was added to an aliquot of 100 µl (10$^7$) protoplasts, mixed and incubated for 25 minutes on ice. PEG was added in two 200 µl aliquots and an 850 µl aliquot, and the mixture was incubated at room temperature for 20 minutes. Finally, the mixture was washed with 10 ml of STC, harvested by centrifugation at 2000 rpm for 10 minutes at room temperature and the sample was plated on a MM plate containing 100 µg/ml hygromycin for selection of transformants.

For A. tumefaciens transformation, a 100 µl aliquot containing 3×10$^6$ to 10$^7$ protoplasts was mixed with 100 µl A. tumefaciens grown as described in Materials and Methods. From this sample ⅒, ¹⁄₁₀₀ and ¹⁄₁₀₀₀ dilutions were made in IM. Subsequently, the mixtures were plated on nitrocellulose filters placed on IM plates containing 5 mM glucose and incubated at room temperature or 29° C. for 2 days. Hereafter, the filters were transferred to Aspergillus MM plates containing 200 µM cefotaxim to kill the Agrobacterium cells and 100 µg/ml hygromycin to select for transformants. Three separate experiments were carried out with A. tumefaciens containing the binary vector pURS750. In each experiment transformations were carried out in duplo and a negative control without AS was included. The results are depicted in Table 3 below. Transformed hygromycin resistant cells were only obtained in medium containing AS. The negative controls never gave rise to transformed cells. These results demonstrate unequivocally that induction of the vir genes is essential for transfer of the T-DNA to the mould cell and therefore that A. tumefaciens is capable of transforming the mould Aspergillus awamori. The transformation frequency varied from approximately 300 to 7200 transformants per 10$^7$ protoplasts, which is much higher than the values for PEG transformation obtained in earlier non-published experiments. For PEG transformations with pAN7.1 (containing the same expression cassette with the hygromycin gene as selectable marker, which is also present in pUR5750, see Materials and Methods) up to 18 transformants per µg per 10$^7$ protoplasts were obtained. This is in agreement with the value of about 12 transformants/µg vector DNA published by Ward et al. (see above).

These data demonstrate that by using *A. tumefaciens*-mediated mould transformation up to 400 times more transformants can be generated than with PEG transformation (per µg per $10^7$ protoplasts).

Moreover, in experiment 3 (see Table 3 below) a direct comparison was made between both transformation methods using the same batch of protoplasts. In two PEG transformations, using 5 µg of pAN7.1 per transformation of $10^7$ protoplasts, 6 and 16 transformants were obtained, respectively. On average this is 2.2 transformants per µg per $10^7$ protoplasts. Using *A. tumefaciens* transformation 300 and 480 transformants per $10^7$ recipient cells were obtained, thus on average 390 transformants per $10^7$ recipient cells.

So, by applying a process according to the invention using *A. tumefaciens* transformation about 180 times more transformants were obtained.

TABLE 3

Transformation of moulds using Agrobacterium tumefaciens

| Mould species | Plasmid present in Agrobacterium strain LBA1100 | Experiment | Medium | No. of protoplasts or conidia | No. of Hyg ® transformants | No of Hyg ® transformants per $10^7$ recipients |
|---|---|---|---|---|---|---|
| *Aspergillus awamori* | pUR5750 | 1. | -AS | $3 \times 10^6$ protoplasts | 0 | 0 |
| | | | +AS | $3 \times 10^6$ protoplasts | 100 | 333 |
| | | | +AS | $3 \times 10^6$ protoplasts | 197 | 657 |
| | | 2. | -AS | $3 \times 10^6$ protoplasts | 0 | 0 |
| | | | +AS | $3 \times 10^6$ protoplasts | 1200 | 3960 |
| | | | +AS | $3 \times 10^6$ protoplasts | 2170 | 7233 |
| | | 3. | -AS | $1 \times 10^7$ protoplasts | 0 | 0 |
| | | | +AS | $1 \times 10^7$ protoplasts | 480 | 480 |
| | | | +AS | $1 \times 10^7$ protoplasts | 300 | 300 |
| | pUR5751 | 1. | -AS | $3 \times 10^6$ protoplasts | 0 | 0 |
| | | | +AS | $3 \times 10^6$ protoplasts | 185 | 617 |
| | | | +AS | $3 \times 10^6$ protoplasts | 255 | 850 |
| | | 2. | -AS | $3 \times 10^6$ protoplasts | 0 | 0 |
| | | | +AS | $3 \times 10^6$ protoplasts | 285 | 950 |
| | | | +AS | $3 \times 10^6$ protoplasts | 170 | 567 |
| | pUR5750 | 1. | -AS | $1 \times 10^6$ conidia | 0 | 0 |
| | | | +AS | $1 \times 10^6$ conidia | 100 | 1000 |
| | | 2. | -AS | $1 \times 10^7$ conidia | 0 | 0 |
| | | | +AS | $1 \times 10^5$ conidia | 20 | 2000 |
| *Aspergillus nidulans* | pUR5750 | | -AS | $1 \times 10^7$ conidia | 0 | 0 |
| | | | +AS | $1 \times 10^7$ conidia (a) | 2 | 2 |
| *Aspergillus niger* | pUR575O | | -AS | $1 \times 10^7$ conidia | 0 | 0 |
| | | | +AS | $1 \times 10^7$ conidia (a) | 5 | 5 |
| *Colletotrichum gloeosporioides* | pUR575O | | -AS | $1 \times 10^6$ conidia | 0 | 0 |
| | | | +AS | $1 \times 10^6$ conidia (a) | 130 | 1300 |
| | | | +AS | $1 \times 10^5$ conidia (a) | 5 | 500 |
| *Fusarium graminearum* | pUR575O | 1. | -AS | $4 \times 10^5$ conidia | 0 | 0 |
| | | | +AS | $4 \times 10^5$ conidia | 1 | 25 |
| | | 2. | -AS | ( Freeze dried | 0 | 0 |
| | | | +AS | ( ATCC culture | 5 | ND |
| *Fusarium solani pisi* | pUR575O | | -AS | $1 \times 10^7$ conidia | 0 | 0 |
| | | | +AS | $1 \times 10^7$ conidia | 1 | 1 |
| *Neurospora crassa* | pURS75O | 1. | -AS | $1 \times 10^5$ conidia | 0 | 0 |
| | | | +AS | $1 \times 10^5$ conidia | 50 | 5000 |
| | | 2. | -AS | $1 \times 10^5$ conidia | 0 | 0 |
| | | | +AS | $1 \times 10^5$ conidia | 50 | 5000 |
| *Pleurotus ostreatus* | pUR575O | 1. | -AS | $1.25 \times 10^7$ conidia | 0 | 0 |
| | | | +AS | $1.25 \times 10^7$ conidia | 60 | 48 |
| | | 2. | -AS | $2.5 \times 10^7$ conidia | 0 | 0 |
| | | | +AS | $2.5 \times 10^7$ conidia | 120 | 48 |
| *Trichoderma reesei* | pUR575O | | -AS | $1 \times 10^7$ conidia | 0 | |
| | | | +AS | $1 \times 10^7$ conidia | 240 | 2400 |
| | | | +AS | $1 \times 10^5$ conidia | 12 | 1200 |
| *Agaricuts bisporus* | pUR575O (b) | | -AS | $3 \times 1.2 \times 10^7$ conidia | 0 | 0 |
| | | | +AS | $5 \times 1.2 \times 10^7$ conidia | 10 | 1.6 |

(a) In these experiments selection was not stringent enough. The transformation frequency is based on the number of transformants that survived the second selection on Hygromycin (see also Examples)
(b) Plasmid pUR575O was present in Agrobacterium strain LBA1126 instead of strain LBA1100

In experiments 1 and 2 the plating efficiency (% surviving cells related to number of starting cells) was determined by plating $1/1000$ and $1/10,000$ dilutions on MM plates without hygromycin. In experiment 1 the plating efficiency was 5% and in experiment 2 it was 2.6%.

The Hyg resistant phenotype of transformants was confirmed for 78 randomly picked transformants by streaking the conidia on MM plates containing 200 µM cefotaxim and 100 µg/ml hygromycin. From eight of these transformants, conidia from individual colonies were streaked again on MM plates containing 100 µg/ml hygromycin. This was repeated twice. Subsequently conidia were isolated and cultures were grown to obtain mycelium for genomic DNA isolation. DNA isolation and Southern analysis is described in Materials and Methods. The genomic DNA was digested with BglII or HindIII. BglII does not cut within the T-DNA, therefore this digestion will generate a fragment encompassing the whole T-DNA and the chromosomal sequences flanking both the right and left border sites of the T-DNA. This fragment will be at least 7.5 kb. HindIII cuts once in the T-DNA and the pAN7.1 probe detects only the T-DNA fragment carrying the hygromycin expression cassette and the chromosomal sequences flanking the left T-DNA border. This fragment will be at least 5 kb. Undigested DNA was included in order to confirm the presence of the T-DNA in the high molecular weight chromosomal DNA. Non-transformed mould was used as a negative control. In all eight transformants the T-DNA was integrated at a single chromosomal locus. Seven out of the eight also contained a single T-DNA integration. In one case the T-DNA was integrated as a tandem repeat. With the undigested DNA samples the hybridization signal coincides with the high molecular weight DNA, which confirms T-DNA integration into the chromosome.

Transformations with A. tumefaciens were performed not only with the binary vector pUR5750, but also with the binary vector pUR5751 (see FIG. 2). This vector contains the plasmid replicator AMA1 from Aspergillus nidulans. Plasmids carrying the AMA1 replicon are capable of autonomous maintenance in Aspergillus nidulans. Therefore, this T-DNA should be able to yield a transformed cell wherein the T-DNA is present as an extrachromosomal element. The results of two experiments are depicted in Table 3 above. The transformation frequency varied from approximately 300 to 950 transformants per $10^7$ protoplasts. The Hyg resistant phenotype of transformants was confirmed for 20 randomly picked transformants by streaking the spores on MM plates containing 100 µg/ml hygromycin.

Example 2

Transformation of Aspergillus awamori Conidia

For A. tumefaciens transformation of Aspergillus awamori conidia, a 100 µl aliquot containing $10^7$ conidia was mixed with 100 µl A. tumefaciens grown as described in Materials and Methods. From this sample ¹⁄₁₀ or ¹⁄₁₀₀ dilutions were made in IM. Subsequently, the mixtures were plated on nitrocellulose filters placed on IM plates containing 5 mM glucose and incubated at room temperature for 2 days. Hereafter, the filters were transferred to Aspergillus MM plates containing 200 µM cefotaxim to kill the Agrobacterium cells and 100 µg/ml hygromycin to select for transformants. The results of two experiments are depicted in Table 3 above. Also in this case transformation depended on induction of the vir genes by AS. The transformation frequency varied from approximately 1000 to 2000 transformants per $10^7$ conidia, which is in the same range as the frequency after protoplast transformation. The Hyg resistant phenotype of transformants was confirmed for 15 randomly picked transformants by streaking the conidia on MM plates containing 200 µM cefotaxim and 100 µg/ml hygromycin.

Example 3

Transformation of Aspercillus nidulans conidia

For A. tumefaciens transformation of Aspergillus nidulans conidia, a 100 µl aliquot containing $10^7$ conidia was mixed with 100 µl A. tumefaciens grown as described in Materials and Methods. The mixtures were plated on nitrocellulose filters placed on IM plates containing 5 mM glucose and incubated at room temperature for 2 days. Hereafter, the filters were transferred to Aspergillus minimal medium plates containing 200 µM cefotaxim to kill the Agrobacterium cells and 1000 µg/ml hygromycin to select for transformants. The filter was overlaid with MM agar containing cefotaxim and hygromycin at the same concentrations.

With Aspergillus nidulans selection proved to be cumbersome. Apparently, during co-cultivation the conidia germinated and grew out too far to allow a stringent selection. This observation is in accordance with results obtained by Cullen et al. (Gene 57 (1989) 21–26). They determined that the incubation time before starting selection is very important for a good result. An incubation period of more than 16 hours before selection was applied, resulted in significant background growth, whereas after such incubation period of only 8 hours no colonies were observed. The reported figures were obtained after such incubation period of 12 hours. They also observed a substantial strain variability with respect to hygromycin sensitivity. In view of the results of Cullen et al. the transformation frequency of this Example may be improved by optimising the incubation period before applying the selection.

The result is depicted in Table 3 above. In total 15 putative transformed colonies were obtained. Moreover, the negative control yielded three growing and sporulating colonies. In order to confirm the transformed phenotype, conidia were streaked on MM plates containing 200 µM cefotaxim and 1000 µg/ml hygromycin. The negative controls did not grow and only 2 out of the 15 putative transformants could grow. Therefore, also in this case transformation depended on induction of the vir genes by AS.

Literature data on PEG transformations using the hygromycin resistance gene show transformation frequencies of 5–20 transformants per µg vector DNA (Cullen et al.; Gene 57, (1989) 21–26; Punt et al.;, Gene 56 (1987) 117–124). Using another selectable marker, the argB gene, Fungaro et al. (FEMS Microbiology Letters 125, (1995) 293–298) obtained up to 81 transformants per µg vector DNA, whereas 20–300 transformants per µg vector DNA were obtained with the trpC gene as the marker (Yelton et al. Proc. Natl. Acad. Sci. USA 81 (1984) 1470–1474). These literature data suggest that the number of transformants, that can be obtained using Agrobacterium transformation, can be improved by using another selectable marker gene.

Example 4

Transformation of Aspergillus niger Conidia

For A. tumefaciens transformation of Aspergillus niger conidia, a 100 µl aliquot containing $10^5$, $10^6$ or $10^7$ conidia was mixed with 100 µl A. tumefaciens grown as described in Materials and Methods. The mixtures were plated on nitrocellulose filters placed on IM plates containing 5 mM glucose and incubated at room temperature for 2 days. Hereafter, the filters were transferred to Aspergillus minimal medium plates containing 200 µM cefotaxim to kill the Agrobacterium cells and 200 µg/ml hygromycin to select for transformants. In general, selection proved to be cumbersome. Apparently, during co-cultivation the conidia germinated and grew out too far to allow a stringent selection. This could be improved to some extent by using an overlay on the filter consisting of MM agar containing 200 µM cefotaxim and 200 µg/ml hygromycin.

The results of a typical experiment are depicted in Table 3 above. The experiment yielded 6 growing colonies on the negative control plate and 6 putative transformed colonies on the transformation plates containing AS. In order to confirm the Hyg resistant phenotype of these colonies, conidia from all twelve colonies were streaked on MM plates containing 200 µM cefotaxim and 200 µg/ml hygromycin. Only five out of the six putative transformants grew on the new selection plates. The remaining putative transformant and the colonies from the negative control experiment did not grow. Therefore also in this case transformation depended on induction of the vir genes by AS. Two transformants were subjected to Southern analysis. The genomic DNA was digested with BglII or HindIII. BglII does not cut within the T-DNA, therefore this digestion will generate a fragment encompassing the whole T-DNA and the chromosomal sequences flanking both the right and left border sites of the T-DNA. This fragment will be at least 7.5 kb.

HindIII cuts once in the T-DNA and the probe for the hph gene from pAN7.1 detects only the T-DNA fragment carrying the hygromycin expression cassette and the chromosomal sequences flanking the left T-DNA border. This fragment will be at least 5 kb. Non-transformed mould was used as a negative control. The Southern analysis demonstrated that in both transformants the T-DNA was integrated at a single chromosomal locus, which confirmed the transformed phenotype at the molecular level.

Literature data on PEG-mediated protoplast transformations using the hygromycin resistance gene show transformation frequencies of 5–20 transformants per µg (Punt et al.; Gene 56 (1987) 117–124) and up to 17,000 transformants per µg (Mohr and Esser; Appl Microbiol Biotechnol 34 (1990) 63–70). However, the latter authors mention in their publication: "After colony purification of primary isolates on complete medium, only a few strains (about 10%) grew on hygromycin medium.

Apparently, they had problems with their selection method. For transformation of intact germinating conidia by electroporation using the argB gene, a transformation frequency of 0.5–4 transformants per µg is described (Ozeki et al.; Biosci. Biotech. Biochem. 58 (1994) 2224–2227).

Example 5

Transformation of *Colletotrichum gloeosporioides* Conidia

For *A. tumefaciens* transformation of *Colletotrichum gloeosporioides* conidia, a 100 µl aliquot containing $10^5$ or $10^6$ conidia was mixed with 100 µl *A. tumefaciens* grown as described in Materials and Methods. The mixtures were plated on nitrocellulose filters placed on IM plates containing 5 mM glucose and incubated at room temperature for 2 days. Hereafter, the filters were transferred to Aspergillus minimal medium plates containing 200 µM cefotaxim to kill the Agrobacterium cells and 100 µg/ml hygromycin to select for transformants. After five days incubation at room temperature colonies appeared on the transformation plates.

The transformation with $10^5$ conidia gave 7 transformants, whereas the transformation with $10^6$ conidia gave 175 transformants. No colonies were obtained on the negative control plate. One day later small colonies started to appear on the negative control plate. Apparently, selection was not tight enough to inhibit the growth of non-transformed cells completely. In order to confirm the Hyg resistant phenotype, mycelium from 11 putative transformed colonies and 3 colonies from the negative control was transferred onto MM plates containing 200 µM cefotaxim and 100 µg/ml hygromycin. Eight out of the eleven putative transformants grew on the new selection plates. The three remaining putative transformants and the three colonies from the negative control experiment did not grow. Therefore also in this case transformation depended on induction of the vir genes by AS. The results depicted in Table 3 above are corrected for the false positives that were obtained. Transformation yielded 500 to 1300 transformants per $10^7$ conidia. One transformant was subjected to Southern analysis as described in Example 4. This demonstrated that the T-DNA was integrated at a single chromosomal locus, which confirmed the transformed phenotype at the molecular level.

Stephenson et al. (Aust. Soc. Biochem. Mol. Biol. 26 (1994) Pos-1-31) reported a transformation frequency of less than 100 transformants per µg. Previously, Armstrong and Harris (Phytopathology 83 (1993) 328–332) had reported a transformation frequency of 2–50 transformants per $10^8$ protoplasts when they used benomyl fungicide resistance for selection.

Example 6

Transformation of *Fusarium solani pisi* Conidia

For *A. tumefaciens* transformation of *Fusarium solani pisi* conidia, a 100 µl aliquot containing $10^5$ or $10^7$ conidia was mixed with 100 µl *A. tumefaciens* grown as described in Materials and Methods. The mixtures were plated on nitrocellulose filters placed on IM plates containing 5 mM glucose and incubated at room temperature for 2 days. Hereafter, the filters were transferred to Aspergillus minimal medium plates containing 200 µM cefotaxim to kill the Agrobacterium cells and 100 µg/ml hygromycin to select for transformants. The results are depicted in Table 3 above.

Transformation of $10^7$ conidia gave 1 transformant. No colonies were obtained on the negative control plate. The Hyg resistant phenotype of the transformant was confirmed by growing the transformant on MM plates containing 200 µM cefotaxim and 100 µg/ml hygromycin. Also in this case transformation depended on induction of the vir genes by AS.

When the hygromycin resistance gene was used for PEG transformations of protoplasts, transformation frequencies of 10,000 transformants per µg per $10^7$ protoplasts have been reported for *Fusarium solani* f.sp. cucurbitae race 2 (Crowhurst et al. Current Genetics 21 (1992) 463–469). Transformation of *Fusarium solani* f.sp. phaseoli by PEG and lithium acetate, as reported by Marek et al. (Curr. Genet. 15 (1989) 421–428), yielded 0.2 to 3.3 transformants per µg.

Example 7

Transformation of *Fusarium graminearum* Conidia and Rehydrated Freeze Dried ATCC Material For *A. tumefaciens* transformation of *Fusarium graminearum* conidia, a 100 µl aliquot containing $4 \times 10^5$ conidia was mixed with 100 µl *A. tumefaciens* grown as described in Materials and Methods. Also a rehydrated freeze-dried culture obtained from the American Type Culture Collection was used for transformation. The freeze-dried material, present in a double vial, was rehydrated by the addition of 0.4 ml of sterile water and incubated for 30 minutes at RT. The material that was used for transformation has been stored at 4° C. for approximately two weeks. An aliquot of 100 μl ATCC material was mixed with 200 μl *A. tumefaciens*. The mixtures were plated on nitrocellulose filters placed on IM plates containing 5 mM glucose and incubated at room temperature for 2 days. Half of the ATCC material was co-cultivated on IM plates for five days. Hereafter, the filters were transferred to PDA plates containing 200 μM cefotaxim to kill the Agrobacterium cells and 150 μg/ml hygromycin to select for transformants.

The results are depicted in Table 3 above. Transformation of $4\times10^5$ conidia gave 1 transformant, which is 25 transformants per $10^7$ conidia. For the ATCC material five transformants were obtained when it had been co-cultivated for 5 days. No colonies were obtained on the negative control plate. The Hyg-resistant phenotype of the transformant was confirmed by growing the transformants on PDA plates containing 200 µM cefotaxim and 150 µg/ml hygromycin. Also in this case transformation depended on induction of the vir genes by AS. Two transformants obtained after transformation of the ATCC material were subjected to Southern analysis as described in Example 4. This demonstrated that the T-DNA was integrated at a single chromosomal locus, which confirmed the transformed phenotype at the molecular level.

Transformation of $5 \times 10^6$ to $2 \times 10^7$ protoplasts of *Fusarium graminearum* with the *A. nidulans* acetamidase gene using a PEG transformation method, resulted in transformation frequencies of 5 transformants per µg (Royer et al., Bio/technology 13 (1995), p. 1479–1483).

Example 8

Transformation of *Neurospora crassa* Conidia

For *A. tumefaciens* transformation of *Neurospora crassa* conidia, a 100 µl aliquot containing $10^5$ conidia was mixed with 100 µl *A. tumefaciens* grown as described in Materials and Methods. The mixtures were plated on nitrocellulose filters placed on IM plates containing 5 mM glucose and incubated at room temperature for 2 days. Hereafter, the filters were transferred to Aspergillus minimal medium plates containing 200 µM cefotaxim to kill the Agrobacterium cells and 200 µg/ml hygromycin to select for transformants. The results are depicted in Table 3 above. In the first experiment transformation of $10^5$ conidia gave approximately 50 transformants, whereas the 1/10 dilution gave 5 transformants. In the second experiment transformation of $10^5$ conidia gave also approximately 50 transformants. This means that transformation gives up to 5000 transformants per $10^7$ conidia. The Hyg resistant phenotype of 20 transformants was confirmed by growing the transformants on Aspergillus minimal medium plates containing 200 µM cefotaxim and 200 µg/ml hygromycin. Also in this case transformation depended on induction of the vir genes by AS. Two transformants were subjected to Southern analysis as described in Example 4. This demonstrated that the T-DNA was integrated at a single chromosomal locus, which confirmed the transformed phenotype at the molecular level.

*Neurospora crassa* has been transformed using a variety of methods. Germinating conidia have been transformed by electroporation using the hygromycin resistance gene, transformation frequencies of 3000 to 6000 transformants per µg per $10^7$ conidia were obtained (Chakraborty et al.; Can. J. Microbiol. 37 (1991) 858–863. Lithium acetate transformations of germinating conidia resulted in transformation frequencies of 2 to 10 transformants per µg per $10^7$ conidia (Dhawale et al.; Curr. Gen. 8 (1984) 77–79). PEG transformation of protoplasts resulted in transformation frequencies ranging from 400 to 15.000 transformants per µg (Vollmer and Yanofsky; Proc. Natl. Acad. Sci. USA 83 (1986) 4867–4873).

Example 9

Transformation of *Trichoderma reesei* Conidia

For *A. tumefaciens* transformation of *Trichoderma reesei* conidia, a 100 µl aliquot containing $10^5$ or $10^7$ conidia was mixed with 100 µl *A. tumefaciens* grown as described in Materials and Methods. The mixtures were plated on nitrocellulose filters placed on IM plates containing 5 mM glucose and incubated at room temperature for 2 days. Hereafter, the filters were transferred to Aspergillus minimal medium plates containing 200 µM cefotaxim to kill the Agrobacterium cells and 100 µg/ml hygromycin to select for transformants.

The results are depicted in Table 3 above. Transformation of $10^7$ conidia gave approximately 240 transformants, whereas transformation of $10^5$ conidia gave 12 transformants. This means that the transformation frequency varies between 240 and 1200 transformants per $10^7$ conidia. The Hyg resistant phenotype of 9 transformants was confirmed by growing the transformants on Aspergillus minimal medium plates containing 200 µM cefotaxim and 100 µg/ml hygromycin. Also in this case transformation depended on induction of the vir genes by AS.

Two transformants were subjected to Southern analysis as described in Example 4. This demonstrated that the T-DNA was integrated at a single chromosomal locus, which confirmed the transformed phenotype at the molecular level.

When the same hygromycin selectable marker gene (pAN7.1) is used for PEG transformation of protoplasts, approximately 100 transformants per µg per $10^7$ protoplasts were obtained (Mach et al.; Current Genetics 25 (1994) 567–570). When the hygromycin gene was flanked by homologous expression signals, derived from *Trichoderma reesei* itself, Mach et al. reported increased transformation frequencies of 1800 to 2500 transformants per µg per 1 protoplasts. Similar results were reported by Gruber (Curr. Genet. 18 (1990) 447–451). Using heterologous vectors they obtained about 800 to 1500 transformants per µg. A vector containing the homologous pyrG gene yielded up to 12.000 transformants per µg.

Example 10

Transformation of *Pleurotus ostreatus* Conidia

Few publications are known on the transformation of edible mushrooms. Peng et al. (Curr. Genet. 22 (1992) 53–59) succeeded in transforming *Pleurotus ostreatus*, but the transformed strains were unstable. However, recently Yanai et al. (Biosci. Biotech. Biochem. 60 (1996) 472–475) obtained stable transformants of *Pleurotus ostreatus*.

For *A. tumefaciens* transformation of *Pleurotus ostreatus* conidia, two procedures have been used. In experiment 1 an aliquot of $1.25 \times 10^7$ conidia was mixed with 150 µl *A. tumefaciens* grown as described in Materials and Methods. The mixture was plated on a nitrocellulose filter placed on an IM plate containing 5 mM glucose. In experiment two $2.5 \times 10^7$ conidia were plated on a nitrocellulose filter placed on a PDA plate and pre-incubated for 4 days at room temperature. Subsequently, the filters were transferred to a petri dish, submerged in 25 ml of Agrobacterium culture in IM (grown for 6 hours as described in Materials and Methods) and incubated for 1 hour at room temperature. Hereafter, the filter was placed on an IM plate containing 5 mM glucose. The plates were incubated at room temperature for 3 or 6 days. Hereafter, the filters were transferred to PDA plates containing 200 µM cefotaxim to kill the Agrobacterium cells and 75 µg/ml hygromycin to select for transformants. The results after 6 days co-cultivation are depicted in Table 3 above. Transformation of $10^7$ conidia resulted in approximately 48 transformants.

When conidia were used directly for transformation, transformants were only obtained after 6 day co-cultivation (experiment 1). However, when the conidia had been pre-incubated for 4 days prior to transformation (experiment 2), transformants were obtained after 3 and 6 days of co-cultivation, although after 3 days the number of transformants was lower than after 6 days: 10 instead of 48. Also in this case transformation depended on induction of the vir genes by AS.

When the same hygromycin selectable marker gene (pAN7.1) is used for PEG transformation of protoplasts, approximately 5–46 transformants per µg per $10^7$ viable protoplasts were obtained (Peng et al.; Current Genetics 22 (1992) 53–59). Using bialaphos as a dominant selectable marker Yanai et al. (Biosci. Biotech. Biochem. 60 (1996) 472–475) obtained about 2 transformants per µg.

Example 11

Transformation of *Agaricus bisporus* Conidia

For *A. tumefaciens* transformation of *Agaricus bisporus* conidia from the commercial strain Horst U1 (purchased from "Proefstation voor de Champignoncultuur", P.O. Box 6042, 5960 AA Horst, The Netherlands) were used. The following media were used to germinate the conidia. A Maltextract agar (MOx; 50 gr/l including Maltextract, mycological peptone and agar) purchased from Oxoid or a Maltextract agar as specified by the "Proefstation voor de Champignoncultuur" (MPrf; 2% Maltextract, 10 mM MOPS, 1.5% agar, pH 7.0 with KOH). About $1.2 \times 10^7$ conidia were plated on a nitrocellulose filter placed on either MOx or MPrf medium. An *Agaricus bisporus* breeding-granule (also purchased from "Proefstation voor de Champignoncultuur") was placed on the agar surrounding the filter in order to facilitate germination of the conidia. The petri dishes were sealed with parafilm. The plates were pre-incubated for 5 or 7 days at room temperature. Subsequently, the filters were transferred to a petri dish and submerged in 25 ml of *Agrobacterium tumefaciens* culture in IM (grown for 6 hours as described in Materials and Methods). For transformation the *A. tumefaciens* strain LBA1126 (Bundock et al., EMBO-J. 14 (1995) 3206–3214) was used, in which the binary vector pUR5750 was introduced. This strain LBA1126 was obtained with restrictions on its use from the State University Leiden where Bundock et al. are employed. The filters were incubated for 1 hour at room temperature. Hereafter, the filters were placed on IM plates containing 5 mM glucose and the plates were incubated at room temperature for 5 days. Hereafter, the filters were transferred to MOx or MPrf plates containing 200 µM cefotaxim to kill the Agrobacterium cells and 25 µg/ml hygromycin (Van Rhee et al., Mol Gen Genet 250 (1996) 252–258) to select for transformants. Hygromycin resistant colonies appeared after approximately 5 weeks of incubation. In five transformations 10 transformed colonies were obtained (see Table 3 above). Transformants were obtained with both media and after 5 and 7 days pre-incubation prior to transformation. Also in this case transformation depended on induction of the vir genes by AS. Seven transformants were further cultured on MPrf plates containing 200 µM cefotaxim with or without 25 µg/ml hygromycin. Four transformants were subjected to Southern analysis as described in Example 4. The Southern analysis demonstrated that in all transformants T-DNA was integrated in the chromosomal DNA, which confirmed the transformed phenotype at the molecular level.

The cultivated mushroom *Agaricus bisporus* has recently been transformed by Van Rhee et al. (Mol Gen Genet 250 (1996) 252–258). However, whereas they were able to transform a single homokaryotic strain ATCC 24663 they were not able to directly transform the commercial heterokaryotic strain Horst U1, which strain is widely used for the production of edible mushrooms. For this strain they first had to select a derivative strain that resembled the ATCC 24663 phenotype before they were able to obtain transformants. Therefore application of biotechnology in this species, which is an important crop with a world-wide production of 1.5 million tons in 1990 (Van Rhee et al. Mol Gen Genet 250 (1996) 252–258), was still hampered by the lack of a generally applicable transformation system. The application of biotechnological techniques to mushroom cultivation can greatly improve quality and crop yields.

Example 12

Site-Directed Integration of Multiple Copies of a Gene in *Aspergillus awamori*

Experimental Setup

The experimental design of a process for site-directed integration of multiple copies of a gene in the mould *A. awamori* is shown in FIG. 3. The system is based on two components, (1) a fungal strain containing the pyrG gene with a 3' deletion, and (2) an Agrobacterium strain containing a binary vector suitable for restoring the pyrG gene on recombination. This binary vector contains between the T-DNA borders a repair construct that carries a pyrG gene with a 5' deletion, such that both truncated pyrG genes have part of the pyrG gene in common which functions as one of the recombination sites. The other recombination site must be downstream of the pyrG gene so that on recombination the pyrG gene is restored.

In order to introduce at least one other gene the binary vector should contain multiple copies of at least one gene encoding a desired protein between the two recombination sites, preferably downstream of the truncated pyrG gene. As an alternative one can envisage that recombination with introduction of at least one gene can also occur when the target locus contains a 5' deletion and the repair construct contains the gene(s) to be introduced upstream of a 3' deleted pyrG gene with a second recombination site upstream of the gene(s) to be introduced. However, in that situation care must be taken that the promoter of the pyrG gene is not disturbed.

In order to specifically detect integration by homologous recombination the endogenous pyrG gene was used as a selectable marker gene (Gouka et al., Current Genetics 27 (1995) 536–540).

Construction of the Target Site

Figure 4:
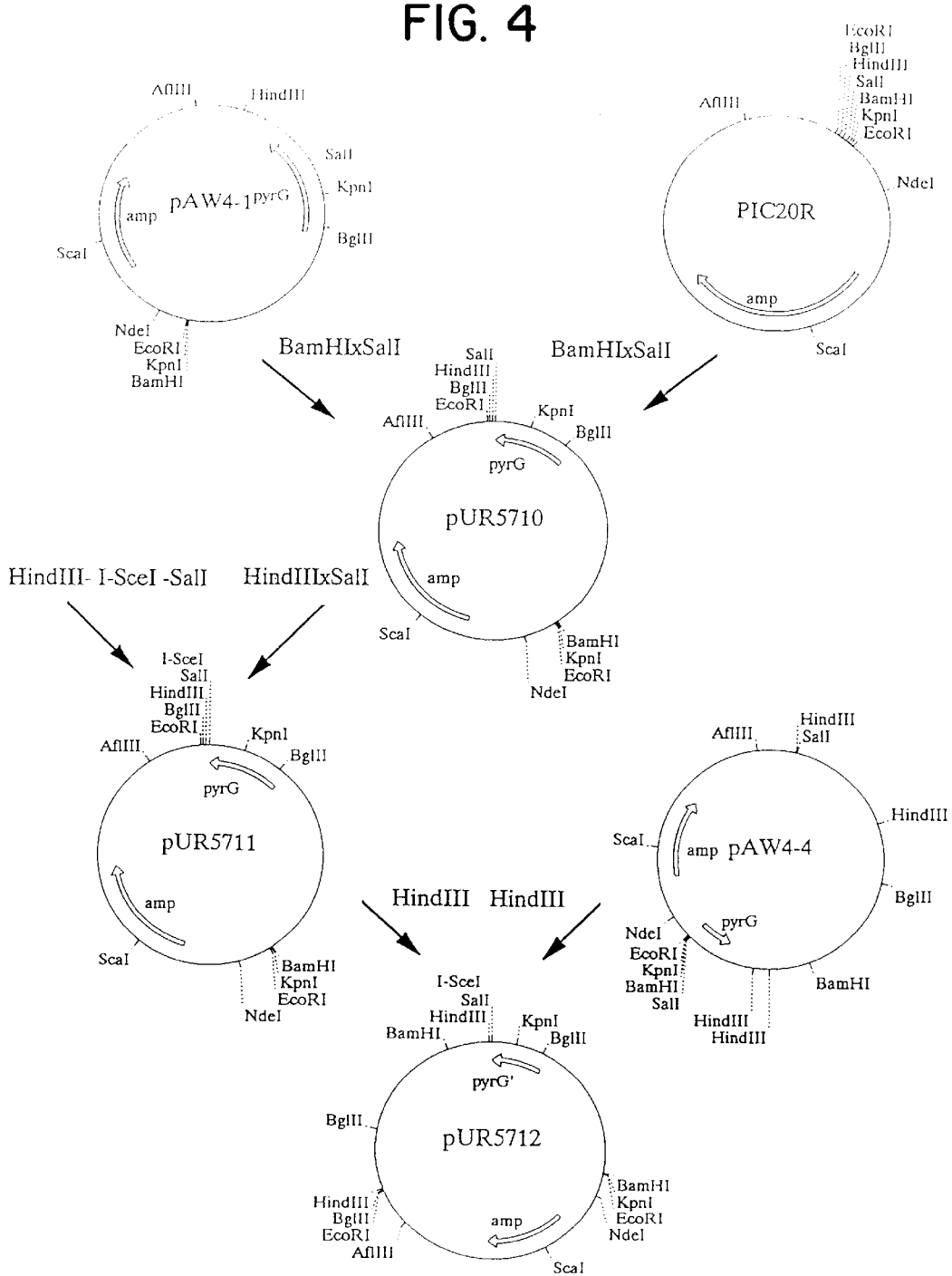
FIG. 4 shows the construction of plasmids pUR5710, pUR5711 and pUR5712. Explanation of the abbreviations used in the construction scheme.

The plasmid pUR5710 (see FIG. 4) was constructed by cloning a 2.0 kb BamHI/SalI fragment containing a 5' part of the pyrG gene, which is present on the plasmid pAW4.1 (Gouka et al.; see above), into the general cloning vector pIC20R (Marsh et al.; Gene 32 (1984) 481–485) digested with BamHI and SalI. Subsequently, a synthetic DNA linker containing the 18 bp recognition site for the I-SceI endonuclease (5'-TAGGGATAACAGGGTAAT-3' SEQ ID NO:1) flanked by SalI and HindIII sites was cloned into the plasmid pUR5710 digested with SalI and HindIII. This resulted in the plasmid pUR5711 (see FIG. 4). The plasmid pUR5712 (see FIG. 4) was constructed by cloning a 2.0 kb HindIII fragment containing sequences downstream of the pyrG coding region, which is present on the plasmid pAW4.4 (Gouka et al.; see above), into the plasmid pUR5711 digested with HindIII. The orientation of this HindIII fragment compared to the coding region of the pyrG gene is identical to the wildtype situation. The plasmid pUR5712 was used to construct the *A. awamori* mutant pyrG⁻ strain AWCSCE.

Construction of the *A. awamori* Mutant pyrG⁻ Strains AWC-SCE

Transformation of the wild-type *A. awamori* strain was performed with a purified (Qiaex gel extraction kit; Qiagen cat. no. 20021) EcoRI fragment obtained from the plasmid pUR5712 containing the mutant pyrG gene with the I-SceI restriction site at the site of the deletion (see FIGS. 3 and 4). Per transformation $2 \times 10^6$ protoplasts were transformed with 10 μg of DNA. Since pyrG⁻ strains are resistant to 5-FOA (5-fluoro-orotic acid; Boeke et al. Mol Gen Genet 197 (1984) 345–346), pyrG⁻ transformants can be selected directly from wildtype strains. Transformants were selected on MM plates (AspA is replaced by AspA-N; 50×Aspa-N= 0.35 M KCl, 0.55 M KH$_2$PO$_4$, pH 6.5 with KOH) supplemented with 10 mM uridine and 0.75 mg/ml of 5-FOA, with 10 mM proline as the N-source. The mutant phenotype of the transformants that were obtained was checked by growing these colonies on MM plates without uridine. Two transformants that were not able to grow without uridine were further analyzed by Southern blot analysis. The observed DNA pattern agreed with the expected pattern for strain AWCSCE.

Construction of a Multi-Copy Vector

Figure 5A:
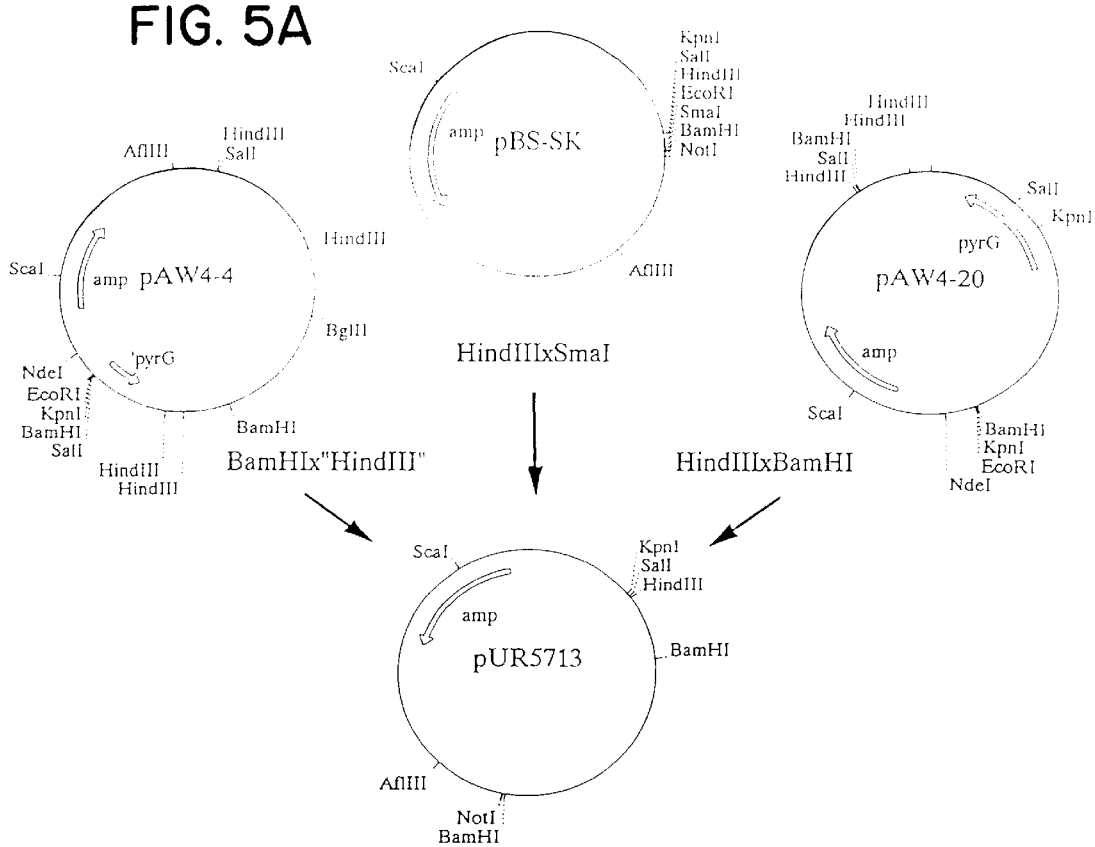
FIG. 5 shows the construction of plasmids pUR5713 (FIG. 5A) and pUR5714 (FIG. 5B). Explanation of the abbreviation used in the construction scheme.

For the construction of the plasmid pUR5713 (see FIG. 5A) plasmid pAW4.4 (see Gouka et al.; see above) was digested with HindIII, the HindIII site was filled in with Klenow and the fragment was subsequently digested with BamHI. The resulting 1.6 kb fragment, containing sequences down stream of the pyrG coding region, was isolated. Furthermore, the plasmid pAW4.20 (Gouka et al.; see above) was digested with BamHI and HindIII and the 0.4 kb fragment, containing sequences present immediately upstream of the 1.6 kb fragment described above, was isolated. The 0.4 kb HindIII/BamHI and 1.6 kb BamHI/filled in HindIII fragments were simultaneously cloned into the general cloning vector pBluescript® SK (Stratagene) digested with HindIII and SmaI. This resulted in the plasmid pUR5713.

Figure 5B:
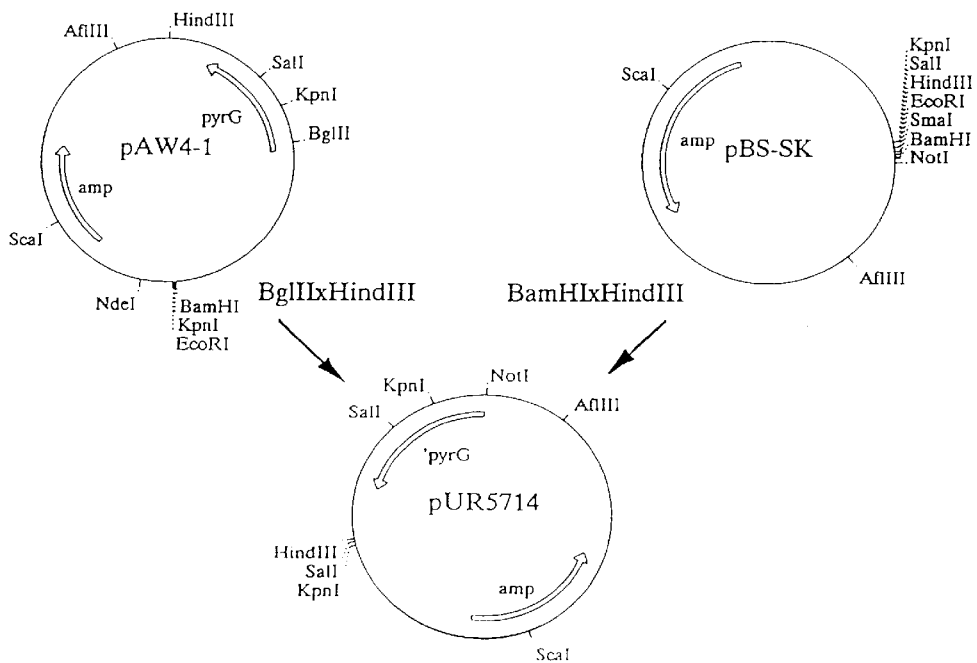
Figure 9:
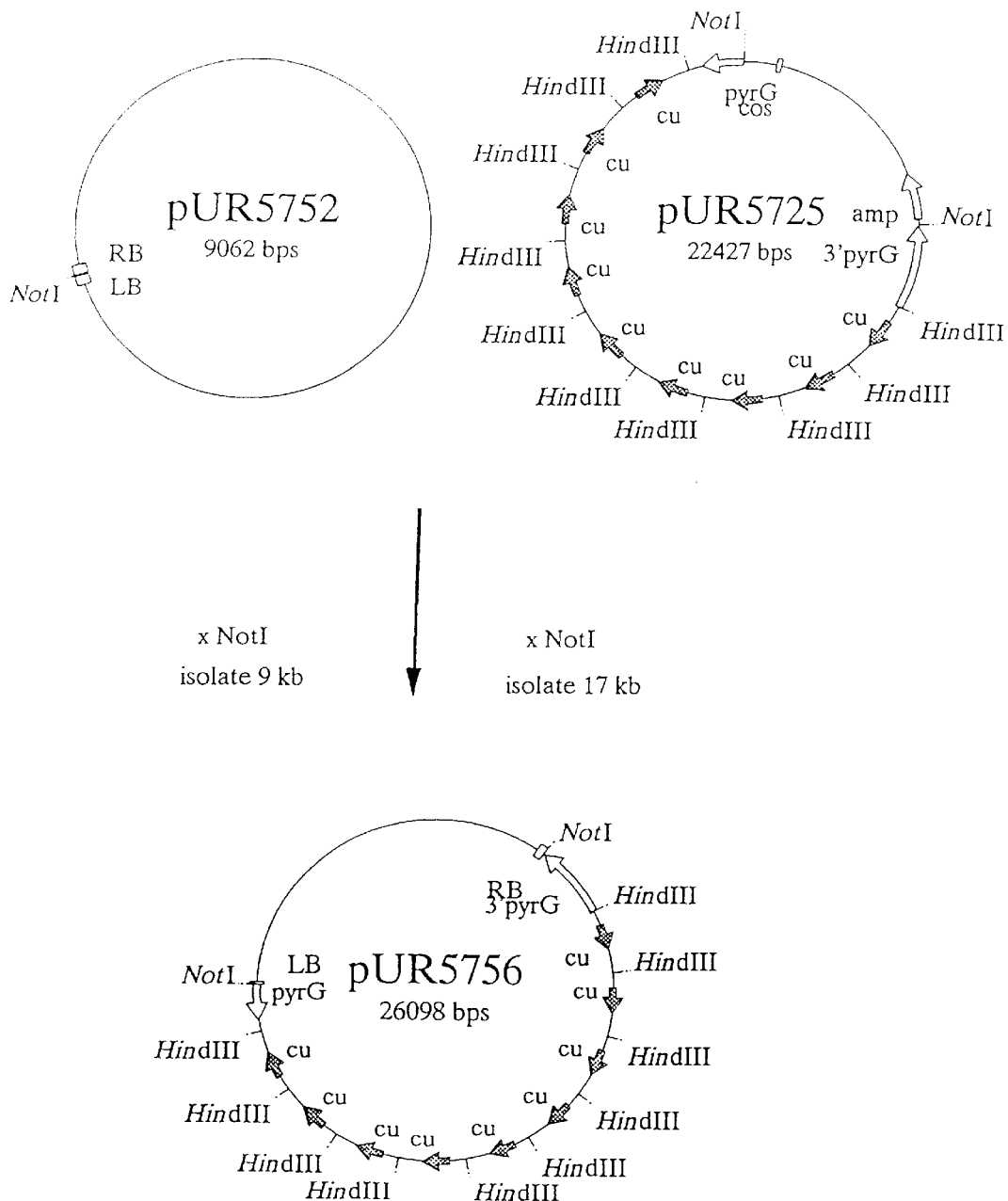
FIG. 9 shows the construction of plasmid pUR5756.

The plasmid pUR5714 (see FIG. 5B) was constructed by cloning a 1.0 kb BglII/HindIII fragment containing a 3' part of the pyrG gene, which is present on the vector pAW4.1, into the general cloning vector pBluescript® SK digested with BamHI and HindIII. The cosmid pUR5716 (see FIG. 9) is derived from the cosmid vector pJB8 (Ish-Horowicz,D. and Burke,J. F.; Nucleic Acids Res 9 (1981) 2989) by replacing the EcoRI/HindIII polylinker fragment by a synthetic linker containing a EcoRI and NotI restriction site having the following sequence:

(5'-AATTC AT GCGGCCGC T-3' SEQ ID NO:2

3'-G TA CGCCGGCG ATCGA-5' SEQ ID NO:3).

Figure 6:
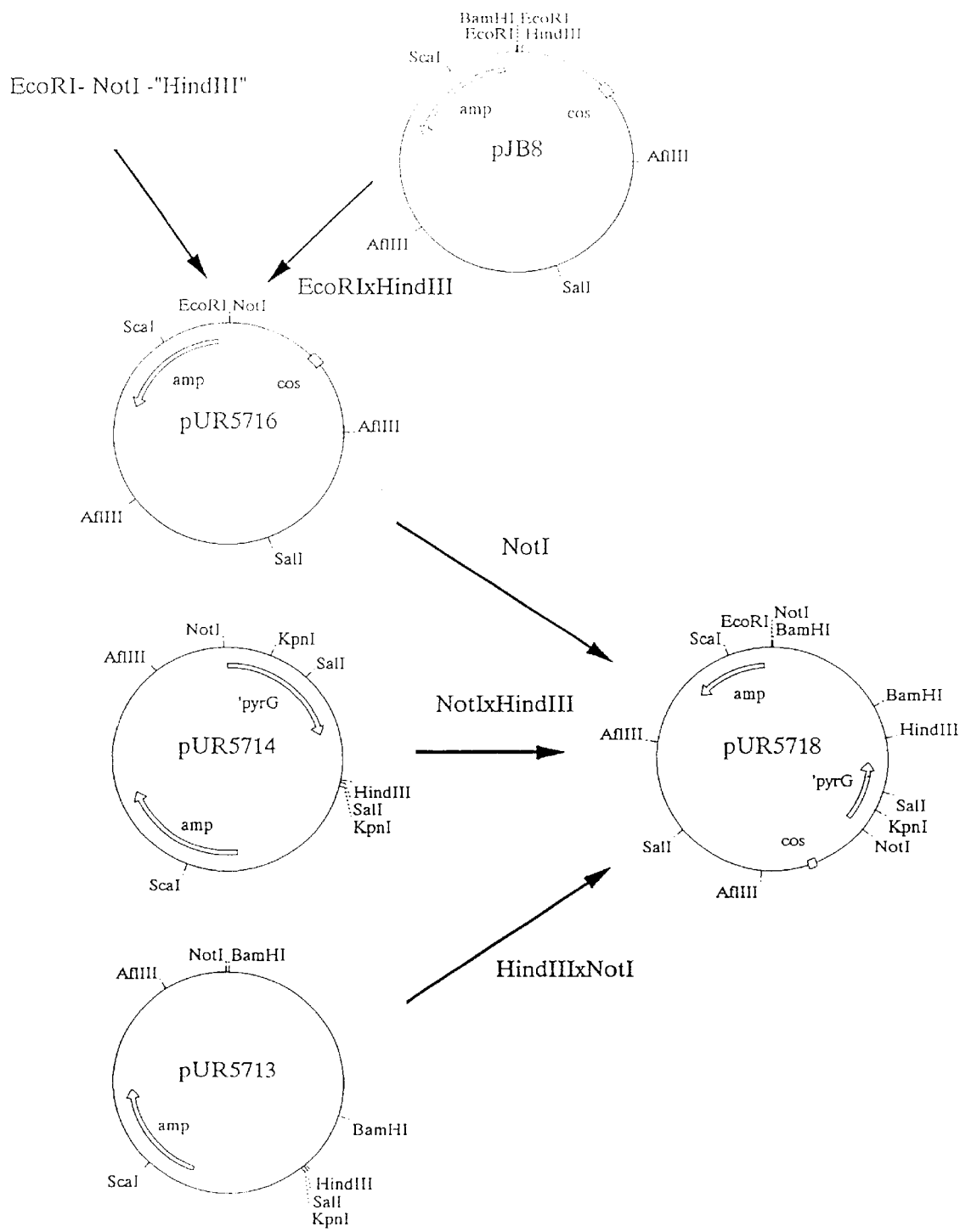
FIG. 6 shows the construction of plasmids pUR5716 and pUR5718. Explanation of the abbreviation used in the construction scheme.

In this cloning step, the HindIII site is lost. The cosmid pUR5718 (see FIG. 6) was constructed by simultanously cloning the 1.0 kb NotI/HindIII fragment from the plasmid pUR5714 and the 2.0 kb HindIII/NotI fragment from the plasmid pUR5713 into the plasmid pUR5716 digested with NotI. Thereby, this vector carries a sequence homologous to both sides of the I-SceI site at the pyrG target locus in the *A. awamori* mutant pyrG⁻ strain AWCSCE.

Figure 7:
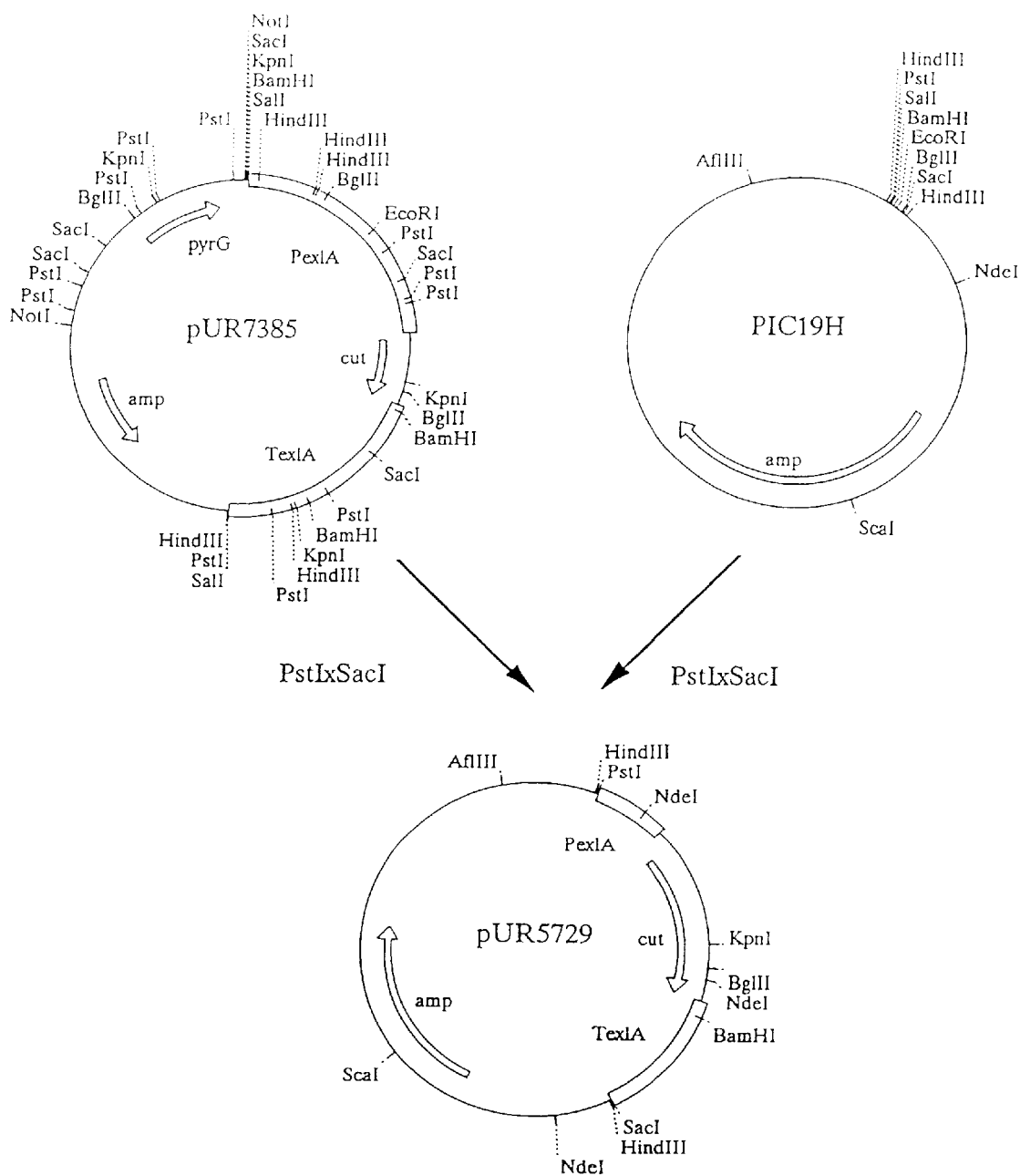
FIG. 7 shows the construction of plasmid pUR5729. Explanation of the abbreviations used in the construction scheme.

The plasmid pUR5729 (see FIG. 7) was constructed by cloning the about 1.5 kb PstI/SacI fragment containing the open reading frame (ORF) of the cutinase gene from *Fusarium solani pisi* (synthetic copy of the CDNA; Van Gemeren et al.; Journal of Biotechnology 40 (1995) 155–162) under control of the promoter and terminator of the exlA gene from *Aspergillus awamori* (Gouka et al.; Applied Microbiology and Biotechnology 46, (1996) 28–35), from the plasmid pUR7385 (Van Gemeren et al.; Applied Microbiology and Biotechnology 45, (1996) 755–763), into the general cloning vector pIC19H (Marsh et al.; see above) digested with PstI and SacI.

Based on the cosmid pUR5718 a new cosmid (pUR5725) was constructed containing multiple copies of the cutinase gene under control of the exlA expression signals (as described above). A single copy of this expression cassette was isolated as a 1.5 kb. HindIII fragment from the plasmid pUR5729 and ligated into the cosmid pUR5718 digested with HindIII. After packaging of the ligation mix using the λ-DNA in vitro packaging module (Amersham; code RPN1717), the packaging mix was transformed into *E. coli* strain 1046 (both according to the protocol provided with the module). From this transformation the cosmid pUR5725 (see FIG. 8) was obtained which contained a tandem array of nine copies of the expression cassette.

In order to produce an *Agrobacterium tumefaciens* vector which can be used for transforming a mould plasmid pUR5752 was constructed. This is a binairy vector with a unique NotI site between the left and right border repeats of the T-DNA and is derived from pSDM14 (R. Offringa; PhD. thesis "Gene targeting in plants using the Agrobacterium vector system"; Leiden University, Leiden 1992) by digestion with KpnI and BamHI and ligation with the following annealed oligonucleotides:

MGANotI: 5'-CAATGCGGCCGCTAAG-3' SEQ ID NO:3

MGANotII:5'-CATGGTTACGCCGGCGATTCCTAG-3' SEQ ID NO:4.

Plasmid pUR5752 was used for introducing into the NotI site multiple copies of the about 1.5 kb fragment with the *Fusarium solanii pisi* cutinase gene controlled by the *A. awamori* endoxylanase promoter and transcription terminator. Therefore, a 17 kb NotI fragment from pUR5725 (see above) containing 9 copies of the cutinase expression cassette was ligated into the NotI site of pUR5752. With this ligation procedure plasmids pUR5756 (see FIG. 9) containing 9 copies of the expression cassette and pUR5755, which contains only 4 copies of the expression cassette (probably due to loss of copies during ligation via intramolecular recombination), were obtained.

As a control plasmid pUR5753 (not containing any cutinase gene) was constructed by cloning a 3.0 kb NotI fragment from pUR5718 (see above) containing the pyrG gene with a 5' deletion and downstream sequences into the NotI site of pUR5752. Plasmid pUR5753 is the same as plasmid pUR5756 except that the 9 copies of the gene between the HindIII sites are absent resulting in a plasmid containing the following elements: left border, NotI site, pyrG gene with 5' deletion, HindIII site, 3' downstream sequences of the pyrG gene, NotI site, right border, Both plasmid pUR5752 and plasmid pUR5753 can be adapted for introducing into the NotI site or HindIII site any homologous or heterologous gene.

Transformation and Analysis of Transformants

For transformation of *A. awamori* strain AWCSCE *A. tumefaciens* strain LBA1126 (Bundock et al., EMBO-J. 14 (1995) 3206–3214; for restrictive use see above) was used containing the binary vectors pUR5753, pUR5755 and pUR5756. The transformation was carried out as described above in Materials and Methods for conidia spores, except that the plates with IM medium additionally contained 1 mM uridine.

Transformants were obtained after about 7 days of incubation. The average transformation frequency with $10^6$ conidia spores was 17 and 30 transformants for pUR5753 and pUR5755, respectively, but only 0.5 transformants for pUR5756. The latter result means that per $10^7$ conidiospores 5 transformants can be obtained with multiple copies of the cutinase expression cassette. This number is remarkably high, since with traditional protoplast transformation it has only been possible to integrate a single copy of a gene at a specific locus, and this with a frequency of approximately only 1–2 transformants per transformation of $10^7$ protoplasts (Gouka et al.; (1995) see above).

A number of transformants were purified twice on Aspergillus minimal medium and conidia spores were isolated from PDA plates. Transformants were subjected to Southern analysis to verify: a) the copy number of the expression cassette, b) the integration site of the expression cassette, and c) whether DNA outside of the T-DNA border repeats was integrated. The genomic DNA was digested with BglII or SalI, fragments were size separated on an 0.7% agarose gel and blotted on a Hybond-N membrane. Hybridization was carried out as described before using an 0.5 kb AflII/SacI fragment containing the A. awamori exlA terminator, which is present in the cutinase expression cassettes, as a probe.

When the DNA was digested with SalI, all transformants contained a hybridizing fragment of about 5 kb which corresponds with the endogenous exlA SalI fragment. Transformants obtained with pUR5755 and pUR5756 appeared to contain a second hybridizing fragment which encompasses all PexlA-cutinase-TexlA expression cassettes. The size is indicative for the number of gene copies present on the fragment. It was found that in the tested strains a variable number of expression cassettes had been integrated. For example, 2 copies were present in strains #8, #9 and #10 transformed with Agrobacterium containing DNA derived from plasmid pUR5755 (originally containing 4 copies), whereas 4 copies were present in strains #13, #14, #15 and #17, 7 or 8 copies in strain #12, and 9 copies in strain #16, all transformed with Agrobacterium containing DNA derived from plasmid pUR5756 (originally containing 9 copies). These results were confirmed by digestion of the DNA with BglII. The latter cuts once in the expression cassette, and therefore all expression cassettes are represented as a single hybridizing fragment of 1.5 kb. The intensity of this hybridizing fragment is indicative for the copy number and was in agreement with the copy numbers given above for the SalI restriction fragments.

Further, all transformants containing the cutinase expression cassette additionally contain a 1.8 kb hybridizing fragment, which is the 5' flanking fragment hybridizing with the probe. The patterns of integration were all compatible with an integration at the pyrG locus. This was also confirmed by hybridization of a similar DNA blot with a 2.4 kb BamHI/HindIII fragment containing the A. awamori pyrG gene. Additionally, a 5 kb hybridizing fragment corresponding to the endogenous exlA gene was present in all transformants. Finally, an 11.9 kb HindIII/EcoRI fragment from pUR5750 containing A. tumefaciens DNA sequences outside the T-DNA border repeats was used to analyze the probable presence of bacterial DNA sequences. None of the transformants showed a hybridization signal which indicates that all are free of bacterial DNA.

In conclusion, it was shown that A. awamori can be transformed with an Agrobacterium tumefaciens strain containing multiple copies of a model gene with frequencies higher than the traditional methods for transformation. Using this system multiple gene copies can be targeted to the pyrG locus without integration of unwanted—bacterial—sequences.

REFERENCES

Ainsworth, Sparrow and Sussman; The Fungi vol IVA+B (1973)

Aldemita and Hodges,; Planta 199 (1996) 612–617

Aleksenko and Clutterbuck; Molecular Microbiology 19 (1996) 565–574

Armstrong and Harris; Phytopathology 83 (1993) 328–332

Beijersbergen et al.; Science 256 (1992) 1324–1327

Bennett and Lasure, Growth media In: Bennett and Lasure (eds) More gene manipulations in fungi, Academic Press, San Diego (1991) 441–458

Bevan; Nucl. Acids Res. 12 (1984) 8711–8721

Bundock et al.; EMBO-Journal 14 (1995) 3206–3214

Bundock & Hooykaas; Proc. Natl. Acad. Sci. USA, 93 (1996) 15272–15275

Chakraborty et al. Can. J. Microbiol. 37 (1991) p. 858–863

Chassy and Flickinger; FEMS Microbiology Letters 44 (1987) 173–177

Crowhurst et al. Current Genetics 21 (1992) 463–469

Cullen et al.; Gene 57, (1989) 21–26

Depicker et al.; Mol. Gen. Genet. 201 (1985) 477–484

Van den Elzen et al.; Plant Molecular Biology 5 (1985) 149–154

Dhawale et al. Curr. Gen. 8 (1984) p. 77–79

Dower et al.; Nucleic Acids Research 16 (1988) 6127–6145

Fincham, J. R. S.; "Transformation in Fungi" published in Microbio-logical Reviews (Mar. 1989) 148–170

Finkelstein, D. B.; "Transformation" (Chapter 6) in the book "Biotechnology of Filamentous Fungi, Technology and Products" (1992) 113–156, edited by Finkelstein and Ball Fungaro et al.; FEMS Microbiology Letters 125, (1995) 293–298

Gams, Van der Aa, Van der Plaats-Niterink, Samson and Stalpers; CBS Course of Mycology 3rd edition (1987)

Gasser and Fraley; Science 244, (1989) 1293–1299

Gietz et al.; Yeast 11 (1995) 355–360

Gouka et al. Current Genetics 27 (1995) 536–540

Gouka et al.; Applied Microbiology and Biotechnology 46, (1996) 28–35

Gruber; Curr. Genet. 18 (1990) 447–451

Hamilton et al.; Proc. Natl. Acad. Sci. USA 93 (1996) 9975–9979

Hanahan, D., 1983, J. Mol. Biol. 166, p.557–580

Herzog et al.; Appl. Microbiol. Biotechnol. 45 (1996) 333–337

Hoekema et al.,; Nature 303 (1983) 179–180

Hooykaas et al.; J. Gen. Microbiol. 110 (1979) 99–109

Hooykaas and Beijersbergen; Annu. Rev. Phytopathol. 32 (1994) 157–179

Hooykaas and Schilperoort; Plant Molecular Biology 19 (1992) 15–38

Hwang et al.; The Plant Cell 7 (1995) 183–193

Ishida et al.; Nature-Biotechnology 14 (1996) 745–750

Jin et al.; J. Bacteriology 169 (1987) 4417–4425

Jin et al.; Molecular Microbiology 7 (1993) 555–562

Lorito et al.; Curr. Genet. 24 (1993) 349–356

Mach et al.; Current Genetics 25 (1994) 567–570

Marek et al.; Curr. Genet. 15 (1989) 421–428

Marsh et al.; Gene 32 (1984) 481–485

Martinelli and Kinghorn; The book "Aspergillus: 50 year on" (1994)

Meilhoc et al.; Bio/Technology 8 (1990) 223–227

Miller et al.; Proc. Natl. Acad. Sci. USA 85 (1988) 856–860

Mohr and Esser; Appl Microbiol Biotechnol 34 (1990) 63–70

Mozo and Hooykaas; Plant Mol. Biol. 16 (1991) 917–918

O'Donnell and Peterson; Chapter 2 in the book "Biotechnology of Filamentous Fungi, Technology and Products" (1992) 7–33, edited by Finkelstein and Ball Ozeki et al.; Biosci. Biotech. Biochem. 58 (1994) 2224–2227

Peng et al.; Curr. Genet. 22 (1992) 53–59

Piers et al.; Proc. Natl. Acad. Sci. USA, 93 (1996) 1613–1618

Punt et al.; Gene 56 (1987) 117–124

Punt and Van den Hondel (Methods in Enzymology 216 (1993) 447–457

Raineri et al.; BIO/TECHNOLOGY 8 (January 1990) 33–38

Risseeuw et al.; Mol. Cell. Biol. 16 (1996) 5924–5932

Royer et al.; Bio/Technology 13 (1995) 1479–1483

Stephenson et al.; Aust. Soc. Biochem. Mol. Biol. 26 (1994) Pos-1–31

Timberlake, W. E. and Marshall, M. A.; Genetic engineering of filamentous fungi; Science 244 (1989) 1313–1317.

Van den Hondel et al.; "Heterologous gene expression in filamentous fungi" (Chapter 18) in the book "More Gene Manipulations in Fungi" (1991) 397–428, edited by Bennett and Lasure Van Gemeren et al.; Applied Microbiology and Biotechnology 45, (1996) 755–763

Van Rhee et al.; Mol Gen Genet 250 (1996) 252–258

Van den Elzen et al.; Plant Molecular Biology 5 (1985) 149–154

Verdoes et al.; Appl. Microbiol. Biotechnol. 43 (1995) 195–205

Volmer and Yanofsky; Proc. Natl. Acad. Sci. USA 83 (1986) 4869–4873

Ward et al.; Experimental Mycology 13 (1989) 289–293

Yanai et al. (Biosci. Biotech. Biochem. 60 (1996) 472–475)

Yelton et al.; Proc. Natl. Acad. Sci. USA 81 (1984) 1470–1474

Zambryski et al.; EMBO-J. 2 (1983) 2143–2150

Information on a deposit of a micro-organism under the Budapest Treaty is given above. In agreement with Rule 28 (4) EPC, or a similar arrangement for a State not being a Contracting State of the EPC, it is hereby requested that a sample of such deposit, when requested, will be submitted to an expert only.

What is claimed is:

1. A process for producing a transformed mould, comprising
   (1) inserting a DNA fragment containing at least one expressable gene to be introduced into a mould into a vector of *Agrobacterium tumefaciens* between the T-DNA borders present in that vector;
   (2) introducing the vector containing the DNA fragment between the T-DNA borders into an *Agrobacterium tumefaciens* strain containing a vir region in its DNA;
   (3) inducing vir genes to release T-DNA containing said DNA fragment from said *Agrobacterium tumefaciens*, and incubating the *Agrobacterium tumefaciens* strain with the mould to be transformed; and
   (4) selecting the transformed mould from the untransformed mould depending on the characteristics of the introduced DNA or its expression product, and optionally culturing the transformed mould.

2. A process according to claim 1, in which the mould belongs to the group of Eumycota.

3. A process according to claim 1, in which the mould is selected from the group consisting of the fungal subdivisions Ascomycotina, Basidiomycotina, Deuteromycotina, Mastigomycotina, and Zygomycotina.

4. A process according to claim 1, in which the DNA fragment contains multiple copies of a desired gene.

5. A process according to claim 1, in which the DNA fragment is integrated in a selected locus of the mould genome.

6. A process according to claim 5, in which the DNA fragment is integrated in the locus of the mould genome for a gene encoding orotidine-5'-phosphate decarboxylase.

7. A process according to claim 5, in which the transformed mould does not contain any *Agrobacterium tumefaciens* DNA sequence.

8. A process according to claim 1, in which the DNA fragment is randomly integrated in the mould genome.

9. A transformed mould obtainable by Agrobacterium mediated transformation as claimed in claim 8 said mould comprising in its genome one or more parts of T-DNA border sequences.

10. A process according to claim 1, in which the mould belongs to the species of *Aspergillus awamori*.

11. A process according to claim 1, in which the mould belongs to the species of *Aspergillus niger*.

12. A process according to claim 1, in which the mould belongs to the species of *Aspergillus nidulans*.

13. A process according to claim 1, in which the mould belongs to the species of *Fusarium solani pisi*.

14. A process according to claim 1, in which the mould belongs to the species of *Fusarium graminearum*.

15. A process according to claim 1, in which the mould belongs to the species of *Trichoderma reesei*.

16. A process according to claim 1, in which the mould belongs to the species of *Colletotrichum gloeosporioides*.

17. A process according to claim 1, in which the mould belongs to the species of *Neurospora crassa*.

18. A process according to claim 1, in which the mould belongs to the species of *Pleurotus ostreatus*.

19. A process according to claim 1, in which the mould belongs to the species of *Agaricus bisporus*.

20. A process according to claim 6, in which said gene encoding orotidine-5'-phosphate decarboxylase is pyrG of *Aspergillus awamori*.

21. A process according to claim 6, in which said gene encoding orotidine-5'-phosphate decarboxylase is pyrA of *Aspergillus niger*.

22. A process according to claim 6, in which said gene encoding orotidine-5'-phosphate decarboxylase is pyr4 of *Neurospora crassa*.

23. A process according to claim 5, in which the transformed mould does not contain a T-DNA border sequence.

* * * * *